US010803578B2

(12) United States Patent
Butte et al.

(10) Patent No.: US 10,803,578 B2
(45) Date of Patent: *Oct. 13, 2020

(54) SYSTEMS AND METHODS FOR RECORDING SIMULTANEOUSLY VISIBLE LIGHT IMAGE AND INFRARED LIGHT IMAGE FROM FLUOROPHORES

(71) Applicant: Cedars-Sinai Medical Center, Los Angeles, CA (US)

(72) Inventors: Pramod Butte, Los Angeles, CA (US); Adam Mamelak, Sherman Oaks, CA (US)

(73) Assignee: Cedars-Sinai Medical Center, Los Angeles, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/195,850

(22) Filed: Jun. 28, 2016

(65) Prior Publication Data

US 2016/0364858 A1 Dec. 15, 2016

Related U.S. Application Data

(63) Continuation of application No. 14/848,132, filed on Sep. 8, 2015, now Pat. No. 9,407,838, which is a (Continued)

(51) Int. Cl.
*G06T 7/00* (2017.01)
*H04N 5/33* (2006.01)
(Continued)

(52) U.S. Cl.
CPC ........ *G06T 7/0012* (2013.01); *A61B 1/00009* (2013.01); *A61B 1/00045* (2013.01);
(Continued)

(58) Field of Classification Search
None
See application file for complete search history.

(56) References Cited

U.S. PATENT DOCUMENTS

| 4,760,441 A | 7/1988 | Kohno et al. | |
| 4,799,754 A * | 1/1989 | Goldenberg | A61B 18/245 385/141 |

(Continued)

FOREIGN PATENT DOCUMENTS

| JP | H10151104 A | 6/1998 |
| JP | H10201707 A | 8/1998 |

(Continued)

OTHER PUBLICATIONS

EP Application No. 14787668.4 Extended Search Report dated Sep. 7, 2016; 7 pages.

(Continued)

*Primary Examiner* — Dakshesh D Parikh
(74) *Attorney, Agent, or Firm* — Wilson Sonsini Goodrich & Rosati

(57) ABSTRACT

The invention provides systems and methods for imaging a sample. In various embodiments, the invention provides a system comprising an image sensor, a laser for emitting excitation light for an infrared or near-infrared fluorophore, a visible light source, a notch beam splitter, a notch filter, a synchronization module, an image processing unit, an image displaying unit, and light-conducting channels. In various embodiments, the present invention provides a system comprising an image sensor, a laser for emitting excitation light for an infrared or near-infrared fluorophore, a laser clean-up filter, a notch filter, a white light source, an image processing unit, an image displaying unit, and light-conducting channels. In accordance with the present invention, the image sensor can detect both visible light and infrared light.

38 Claims, 12 Drawing Sheets

Related U.S. Application Data continuation-in-part of application No. PCT/US2014/035203, filed on Apr. 23, 2014.

(60) Provisional application No. 61/814,955, filed on Apr. 23, 2013, provisional application No. 62/049,312, filed on Sep. 11, 2014.

(51) Int. Cl.

| | | |
|---|---|---|
| *G01J 1/04* | (2006.01) | |
| *G01J 1/44* | (2006.01) | |
| *H04N 5/235* | (2006.01) | |
| *H04N 5/225* | (2006.01) | |
| *A61B 1/04* | (2006.01) | |
| *A61B 1/00* | (2006.01) | |
| *A61B 1/06* | (2006.01) | |
| *A61B 1/07* | (2006.01) | |
| *G01J 3/44* | (2006.01) | |
| *A61B 1/05* | (2006.01) | |
| *G01N 21/64* | (2006.01) | |
| *H04N 9/04* | (2006.01) | |

(52) U.S. Cl.
CPC ...... *A61B 1/00117* (2013.01); *A61B 1/00186* (2013.01); *A61B 1/00188* (2013.01); *A61B 1/042* (2013.01); *A61B 1/043* (2013.01); *A61B 1/05* (2013.01); *A61B 1/063* (2013.01); *A61B 1/0638* (2013.01); *A61B 1/0646* (2013.01); *A61B 1/0669* (2013.01); *A61B 1/07* (2013.01); *G01J 1/0414* (2013.01); *G01J 1/44* (2013.01); *G01J 3/44* (2013.01); *G01N 21/6456* (2013.01); *H04N 5/2252* (2013.01); *H04N 5/2256* (2013.01); *H04N 5/2354* (2013.01); *H04N 5/33* (2013.01); *H04N 5/332* (2013.01); *H04N 9/04* (2013.01); *G01J 2001/448* (2013.01); *G01N 2021/6463* (2013.01)

(56) References Cited

U.S. PATENT DOCUMENTS

| | | | |
|---|---|---|---|
| 5,689,333 A | | 11/1997 | Batchelder et al. |
| 6,075,592 A | | 6/2000 | Banerjee et al. |
| 6,293,911 B1 | | 9/2001 | Imaizumi et al. |
| 7,286,222 B2 | | 10/2007 | Gardner, Jr. et al. |
| 7,538,309 B2 | | 5/2009 | Tanimoto et al. |
| 7,835,012 B1 | | 11/2010 | Schweiger |
| 9,407,838 B2 | | 8/2016 | Butte et al. |
| 2002/0097773 A1 | | 7/2002 | Masui et al. |
| 2002/0113210 A1 | | 8/2002 | Treado et al. |
| 2002/0115908 A1 | | 8/2002 | Farkas et al. |
| 2002/0156380 A1 | | 10/2002 | Feld et al. |
| 2003/0230715 A1* | | 12/2003 | Remillard ............ G02B 23/12 250/330 |
| 2004/0245350 A1 | | 12/2004 | Zeng |
| 2005/0243307 A1 | | 11/2005 | Silcott et al. |
| 2005/0288556 A1* | | 12/2005 | Sugimoto ........... A61B 1/00009 600/160 |
| 2006/0011860 A1 | | 1/2006 | Hecht et al. |
| 2006/0098895 A1 | | 5/2006 | Westphal |
| 2006/0226375 A1 | | 10/2006 | Maruo |
| 2006/0238757 A1* | | 10/2006 | Silcott ............... G01N 15/0618 356/338 |
| 2007/0216898 A1* | | 9/2007 | Gardner, Jr. ............ G01J 3/02 356/301 |
| 2008/0251694 A1 | | 10/2008 | Tanimoto et al. |
| 2009/0050806 A1 | | 2/2009 | Schmidt et al. |
| 2009/0065679 A1 | | 3/2009 | Tanimoto |
| 2010/0091287 A1 | | 4/2010 | Power |
| 2010/0245552 A1* | | 9/2010 | Higuchi ............ A61B 1/00096 348/68 |
| 2010/0245616 A1* | | 9/2010 | Yoshino ............... A61B 1/0638 348/223.1 |
| 2011/0063427 A1 | | 3/2011 | Fengler et al. |
| 2011/0261179 A1 | | 10/2011 | Fomitchov |
| 2011/0270092 A1* | | 11/2011 | Kang ................... A61B 5/0071 600/476 |
| 2012/0026339 A1 | | 2/2012 | Kojima et al. |
| 2012/0104280 A1* | | 5/2012 | Manian ............ G02B 21/0076 250/459.1 |
| 2012/0123205 A1 | | 5/2012 | Nie et al. |
| 2012/0150043 A1 | | 6/2012 | Mahmood et al. |
| 2012/0268573 A1* | | 10/2012 | Schonborn .......... G02B 21/365 348/49 |
| 2013/0041226 A1 | | 2/2013 | McDowall |
| 2013/0096376 A1* | | 4/2013 | Takei ...................... A61B 1/063 600/103 |
| 2014/0187967 A1* | | 7/2014 | Wood .................. A61B 5/0077 600/473 |

FOREIGN PATENT DOCUMENTS

| | | |
|---|---|---|
| JP | 2001178672 A | 7/2001 |
| JP | 2008033263 A | 2/2008 |
| JP | 2009039510 A | 2/2009 |
| JP | 2011528918 A | 12/2011 |
| JP | 2012088304 A | 5/2012 |
| WO | WO-2009117483 A1 | 9/2009 |
| WO | WO-2012043771 A1 | 4/2012 |
| WO | 2014176375 A2 | 10/2014 |

OTHER PUBLICATIONS

PCT/US2014/035203 International Search Report and Written Opinion dated Dec. 24, 2014; 18 pages.
PCT/US2014/035203 International Preliminary Report on Patentability dated Oct. 27, 2015; 14 pages.
Jai's new 2-CCD camera AD-080 CL. Retrieved from www.jai.com (2013); 2 pages.
Shahin et al. Biometric Authentication Using Fast Correlation of Near Infrared Hand Vein Patterns. International Journal of Biological and Life Sciences (2006). 2(3): 141-148.
EP 14787668.4 Extended Search Report dated Sep. 7, 2016, 7 pages.
U.S. Appl. No. 14/848,132, Non-Final Office Action dated Dec. 24, 2015.
U.S. Appl. No. 14/848,132, Notice of Allowance dated Apr. 4, 2016.

\* cited by examiner

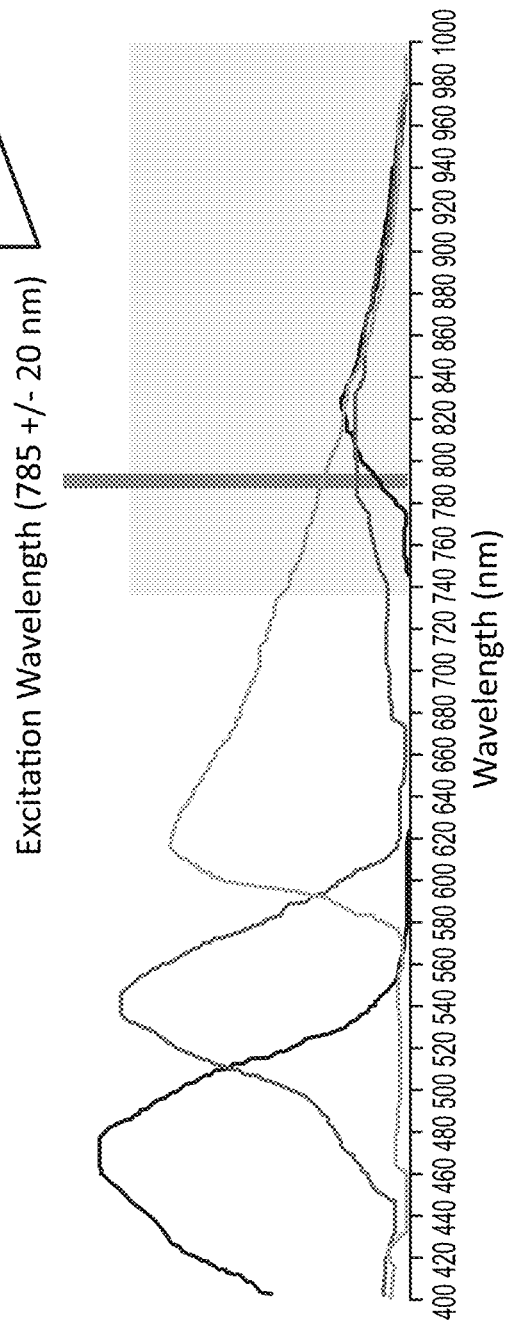

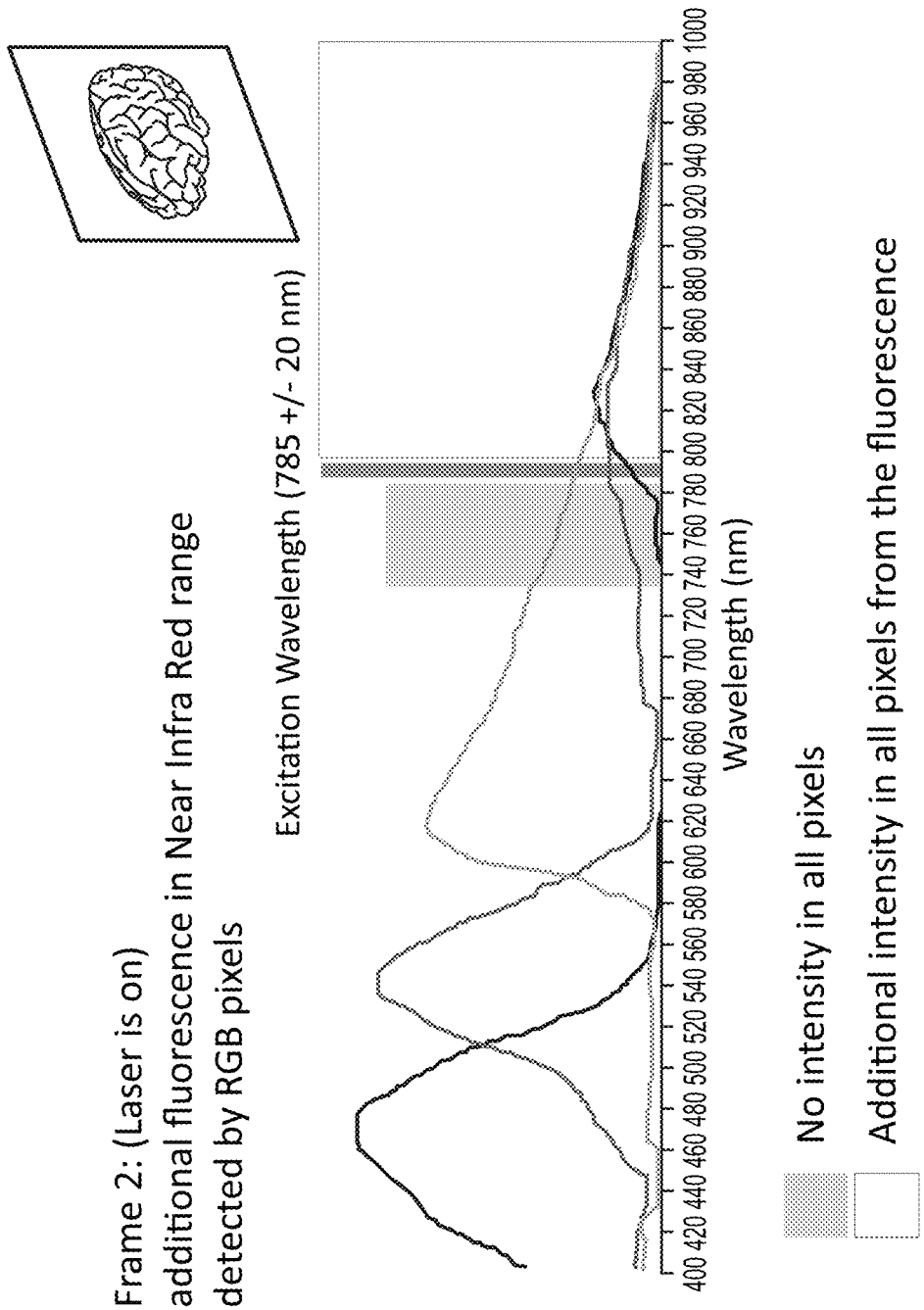

SYSTEMS AND METHODS FOR RECORDING SIMULTANEOUSLY VISIBLE LIGHT IMAGE AND INFRARED LIGHT IMAGE FROM FLUOROPHORES

CROSS-REFERENCE TO RELATED APPLICATIONS

This application is a continuation of U.S. patent application Ser. No. 14/848,132, filed Sep. 8, 2015, now U.S. Pat. No. 9,407,838, issued Aug. 2, 2016, which is a continuation-in-part of International Patent Application No. PCT/US2014/035203, filed Apr. 23, 2014, which designated the U.S., was published under PCT Article 21(2) in English, and claims priority under 35 U.S.C. § 119(e) to U.S. provisional patent application No. 61/814,955, filed Apr. 23, 2013. U.S. patent application Ser. No. 14/848,132 also claims priority under 35 U.S.C. § 119(e) to U.S. provisional patent application No. 62/049,312, filed Sep. 11, 2014. The contents of all the related applications cross-referenced herein are herein incorporated by reference in their entirety as though fully set forth.

FIELD OF INVENTION

The invention provides systems and methods for recording simultaneously visible light image and infrared (IR) light image from fluorophores.

BACKGROUND OF THE INVENTION

All publications cited herein are incorporated by reference in their entirety to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

In recent years, there has been an interest in the use of infrared (IR) dyes for detection of tagged tissue such as tumors and vessels during surgical removal of tumors in a clinical setting. Infrared dyes are considered superior tagging dyes for marking tissue due to their higher penetration depths, lack of auto-fluorescence in that region of spectrum that can add noise to the imaging, and also lack of absorption from hemoglobin (i.e., blood) and water in that region of the spectrum which can reduce the fluorescence signal. To utilize these dyes in, for example, the clinical operating room environment requires an IR sensitive imaging system, which is capable of acquiring high resolution images in the normal white light visible spectrum, while simultaneously acquiring and overlaying the infrared signal on top of normal visible spectrum images in order to provide a contrast to a surgeon while operating.

However, due to the general absence of applications of fluorescent tumor ligands in surgical oncology, currently there are no imaging systems available commercially that are optimized for near infrared (NIR) fluorescence based resection of tumors. The clinical systems that do exist were primarily designed to detect unbound intravascular indocyanine green (ICG), an FDA approved NIR fluorescent dye. ICG is typically intravenously administered in high doses, and imaging is performed 30-60 minutes after injection. The intravascular fluorescent load achieved with this approach is high, and approved clinical imaging devices have adequate sensitivity for these applications. Examples of such systems include a fluorescent module incorporated into operating microscopes (OPMI Pentero Infrared 800, Carl Zeiss) as well at the SPY® and Pinpoint® systems (Novadaq), and the FluoBeam® 800 (Fluoptics) hand-held unit.

These systems have adequate sensitivity for intravascular imaging, but are not practical for use in, for example, targeted tumor-specific NIR fluorescence. For example, Fluobeam is hand held device with no overlay of white light images but is not designed for practical use as a surgical tool that requires HD quality images in white light, maneuverability, magnification, illumination, and automated co-registration of NIR images. One of the reasons for such low sensitivity is due to less fluorescent photons captured by the imaging system, as such systems may principally use one (NIR only) or two (NIR and visible) cameras with a long pass filter. In a simultaneous visible and NIR capture imaging systems, one camera captures the image in the visible spectrum and second camera captures the fluorescent image. This is achieved by splitting the incident light from the field into two channels using a beam-splitter. One beam transmits the NIR fluorescent light to one of the cameras while the other beam of visible light passes through the beam splitter into the second camera. As the fluorescent excitation and emission of NIR dyes such as ICG have a very narrow stokes shift, the long pass filter causes a significant loss of fluorescent light (FIG. 1), and subsequent detection sensitivity. Fluorescence imaging of tumors requires a targeting moiety to attain high specificity, and enable reliable differentiation between cancer tissue and surrounding normal tissues. To achieve this, doses are kept low and the time between drug administration and imaging is quite long (12-48 hours in most cases) to permit uptake of the probe by the tumor and for the washout of unbound material from normal tissues. This results in markedly less fluorescent signal, making currently marketed systems inadequate for detection. Additionally, these systems can be cumbersome to use in the clinical setting, due to the fact that there are two camera attachments, and require a complete change in the existing setup. This inadequacy of the existing systems drives the need for device innovation to take advantage of the specificity of these novel imaging agents.

Accordingly, there is a need for highly sensitive systems and methods that can record simultaneously visible light image and infrared light image from fluorescent dye. The invention described herein meets the unmet need by providing systems and methods for recording simultaneously visible light image and infrared light image from fluorophores.

SUMMARY OF THE INVENTION

Various embodiments of the present invention provide an imaging system for imaging a sample comprising an infrared or near-infrared fluorophore either alone or attached to a targeting moiety such as a peptide, protein, nanoparticle, nanoconjugate, antibody, and nucleic acid (e.g., DNA and RNA strands) or to any other such biologically specific targeting entity. The imaging system comprises: an image sensor, a laser, a laser clean-up filter, a notch filter, and a white light source. The image sensor detects visible light and infrared light and generates sensor signals. The laser emits an excitation light for the infrared fluorophore. The laser clean-up filter is placed in the light path from the laser to the sample, and narrows the wavelength band of the excitation light to the peak absorption band of the infrared or near-infrared fluorophore. The narrowed excitation light excites the infrared or near-infrared fluorophore at the peak absorption in the sample to emit an emission light. The notch filter is placed in the light path from the sample to the image sensor, and blocks the excitation light. The white light source emits a light comprising visible light. In various embodiments, the image sensor is without a NIR long pass filter. In various embodiments, the imaging system further comprises a fast trigger unit.

Various embodiments of the present invention provide an imaging system for imaging a sample comprising an infrared or near-infrared fluorophore. The system comprises: an image sensor, a laser, a notch beam splitter, a notch filter, and a synchronization module. The image sensor detects visible light and infrared light and generates sensor signals. The laser emits an excitation light for the infrared or near-infrared fluorophore and alternates between on and off statuses. The notch beam splitter is placed in the light path from the laser to the sample and in the light path from the sample to the image sensor. The excitation light is reflected by the notch beam splitter to the sample; the excitation light excites the infrared or near-infrared fluorophore in the sample to emit an emission light; and the emission light is transmitted through the notch beam splitter to the image sensor. The notch filter is placed in the light path from the sample to the image sensor, and the notch filter blocks the excitation light. The synchronization (trigger) module synchronizes the image sensor with the laser and visible light, whereby a single sensor signal is synchronized to a single on or off status of the laser.

Also provided is a method of imaging a sample. The method comprises the steps of: providing a sample, providing an imaging system described herein, and imaging the sample with said imaging system.

While various embodiments of the present invention are described in the context of various infrared or near-infrared fluorophores, it should not be construed that the present invention is limited to those infrared or near-infrared fluorophores. In fact, those infrared or near-infrared fluorophores are merely non-limiting examples. Indeed, the present invention may be used for fluorophores in any suitable segment of electromagnetic spectrum, for example, ultraviolet (UV), ultraviolet A, ultraviolet B, ultraviolet C, near ultraviolet, middle ultraviolet, far ultraviolet, hydrogen lyman-alpha, vacuum ultraviolet, extreme ultraviolet, visible, infrared, near infrared, mid infrared, and far infrared. Examples of fluorophores outside the infrared or near-infrared range include but are not limited to fluorescein, sodium yellow, and 5-aminolevulinic acid (5-ALA). While in various embodiments of the present invention, particular types of imaging components (e.g., image sensors, lasers, laser clean-up filters, notch filters, and other associated filters) are described in the context of various infrared or near-infrared fluorophores, it should not be construed that the present invention is limited to those particular imaging components. In fact, those particular imaging components are merely non-limiting examples. Indeed, the present invention also contemplates choosing and including appropriate imaging components (e.g., image sensors, lasers, laser clean-up filters, notch filters, and other associated filters) for the use of those fluorophores outside the infrared or near-infrared range.

While various embodiments of the present invention are described in the context of imaging, diagnosing, and/or treating tumors, it should not be construed that the present invention is limited to such applications. In fact, the present invention may find utility in any and all detection and diagnosis of a tissue difference, i.e., normal vs. abnormal, due to any and all reasons including but not limited to tumor, injury, trauma, ischemia, infection, inflammation, or auto-inflammation. The present invention provides imaging systems and systems for a wide range of applications, including but not limited to, imaging, diagnosing and/or treating tumor tissues, injured tissues, ischemic tissues, infected tissue, and inflammatory tissues. In any situation where a tissue of interest (e.g., a cancerous, injured, ischemic, infected, or inflammatory tissue) is different from the surrounding tissue (e.g., healthy tissues) due to physiological or pathological causes, an infrared or near-infrared fluorophore may be used to differentially label the tissue of interest and the surrounding tissue, and those areas may be imaged with the imaging systems and methods of the present invention to provide visual guidance for appropriate diagnosis and treatment. Therefore, the imaging systems and methods may be used to image, diagnose, and/or treat subjects with various conditions including but not limited to tumors, cancers, traumatic brain injury, spinal cord injury, stroke, cerebral hemorrhage, brain ischemia, ischemic heart diseases, ischemic reperfusion injury, cardiovascular diseases, heart valve stenosis, infectious diseases, microbial infections, viral infection, bacterial infection, fungal infection, and autoimmune diseases. The imaging systems of the present invention may also be used to image normal tissues in a healthy subject, for example, to identify vasculatures.

BRIEF DESCRIPTION OF FIGURES

FIGS. 5A-5C depict, in accordance with various embodiments of the present invention, an exemplar method for simultaneously recording visible light image and infrared light image from fluorescent dye. When the laser is off, the charge coupled device (CCD) camera captures Frame 1, in which Red-Green Blue (RGB) pixel sensors detect visible light but no fluorescence in near infrared range (NIR). When the laser is on, the CCD camera captures Frame 2, in which RGB pixel sensors detect both visible light and additional fluorescence in NIR. The difference of subtracting Frame 1 from Frame 2 represents the additional fluorescence in NIR.

This calculated frame of the additional fluorescence can be given a false color and added back to Frame 1, thereby generating a composite image frame of visible light and infrared light to be displayed to a surgeon. The process can be continuously repeated to show and record a real-time video during surgery.

Figure 6B:
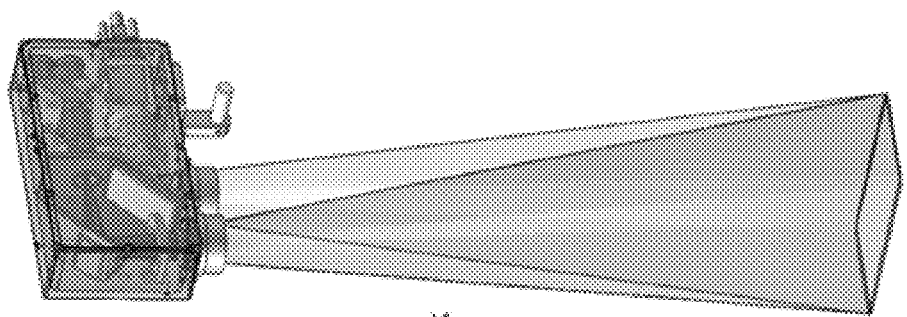
Figure 6A:
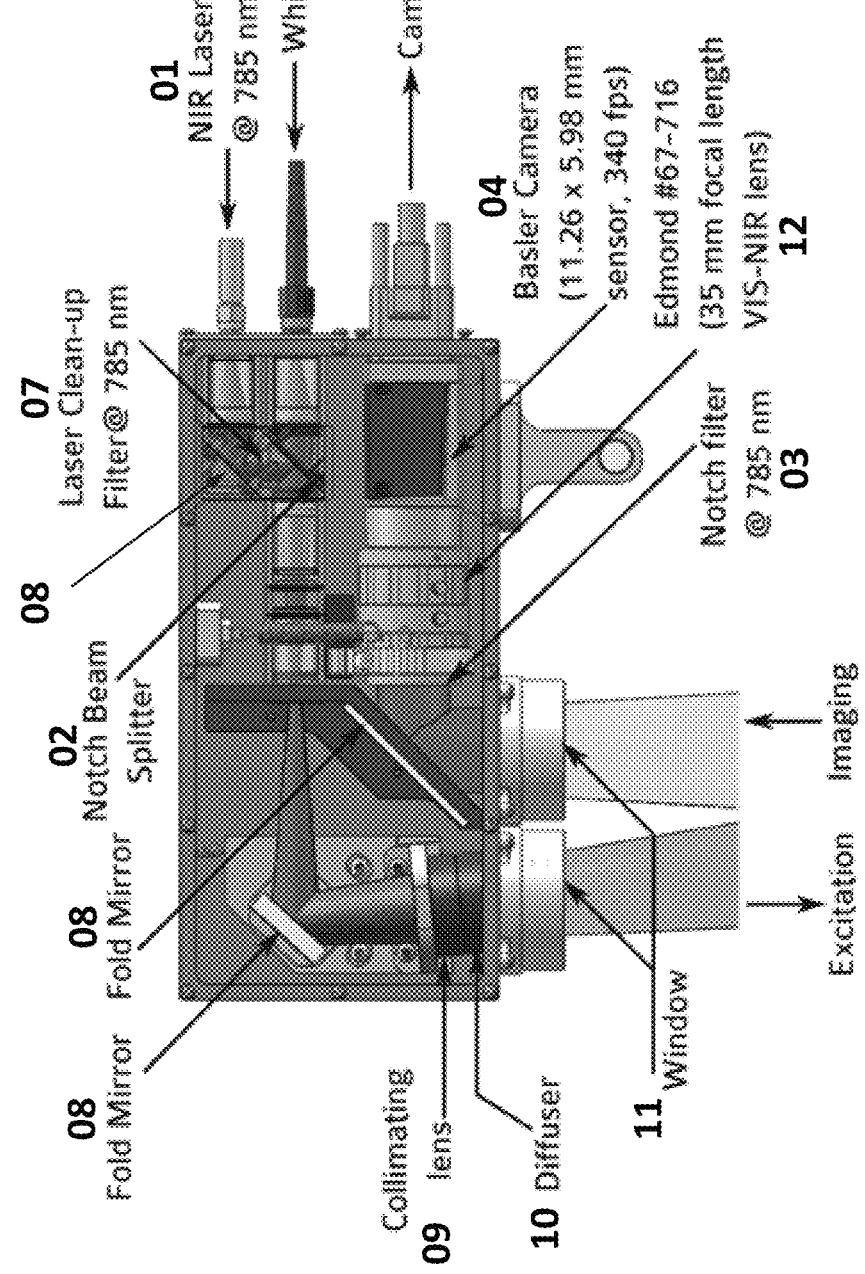
Figure 6C:
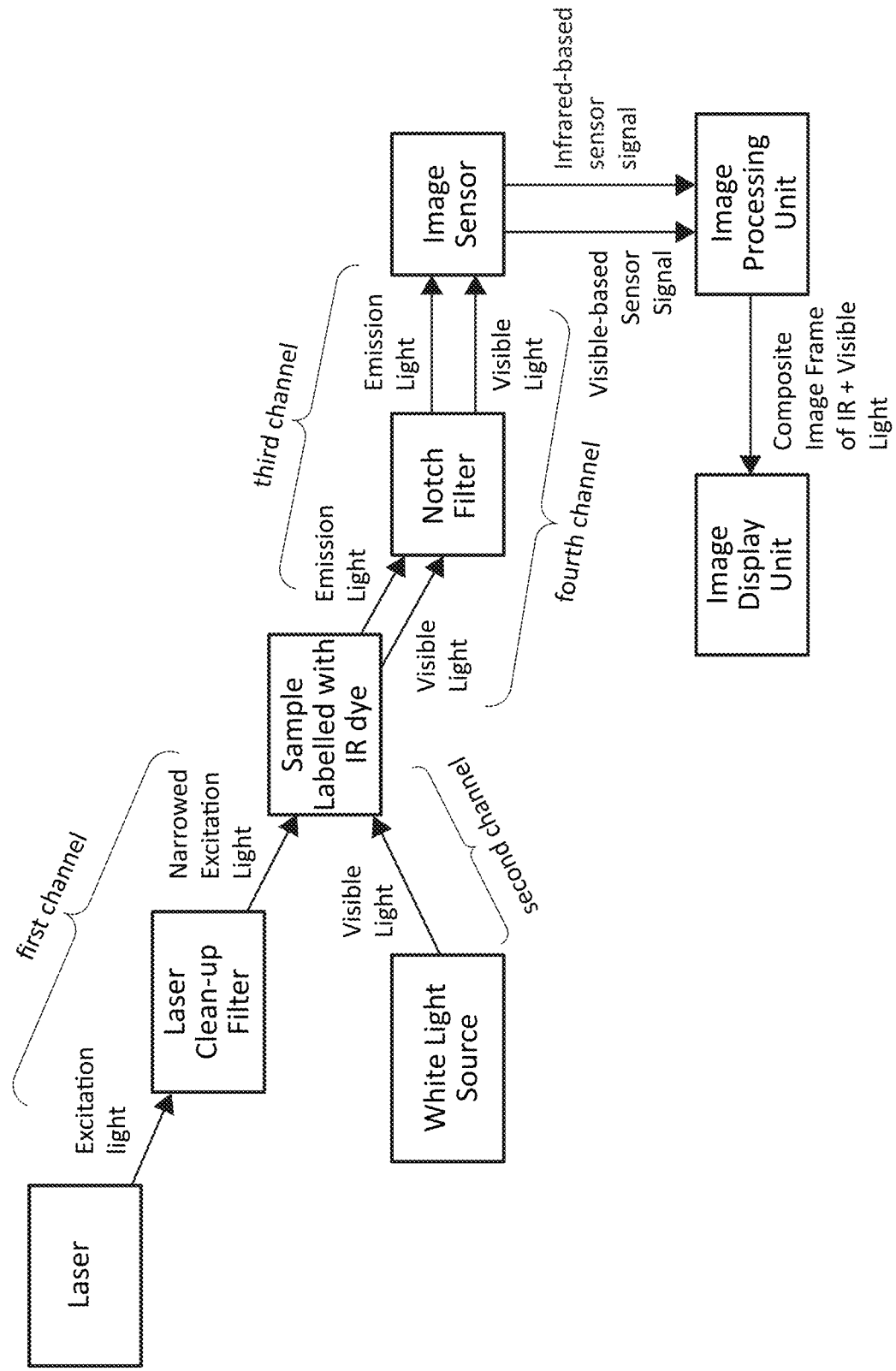

FIGS. 6A-6C depict, in accordance with various embodiments of the present invention, a non-limiting example of clinical prototype. (FIG. 6A) Design and optical specifications. A laser 01 emits an excitation light for an infrared or near-infrared fluorophore. The excitation light travels into the camera and is reflected by a fold mirror 08 to a laser clean-up filter 07. Through the laser clean-up filter 07, the excitation light is narrowed to the excitation wavelength of the infrared or near-infrared fluorophore. The narrowed excitation light is reflected by a notch beam splitter 02, is reflected by another fold mirror 08, passes through a variety of optical components (for example, a collimating lens 09 and a diffuser 10), and exits a window 11 of the camera toward a sample. The narrowed excitation light excites the infrared or near-infrared fluorophore in the sample to emit an emission light. The emission light travels into the camera through another window 11, is reflected by a folder mirror 08 to a notch filter 03, and passes the notch filter 03 and a variety of optical components (for example, a VIS-NIR lens 12). Through the notch filter 03, any excitation light reflected from the sample is blocked. The emission light reaches an image sensor (for example, a camera manufactured by Basler Inc., or any other suitable camera) that detects the emission light and generates a sensor signal. The emission light generated sensor signal is transferred from the camera via a data link to an image processing unit for generating an infrared image frame. A white light source 06 emits a visible light. The visible light travels into the camera, passes a notch beam splitter 02, is reflected by a fold mirror 08, passes through a variety of optical components (for example, a collimating lens 09 and a diffuser 10), and exits a window 11 of the camera toward the sample. The sample is illuminated by the visible light. The visible light travels back into the camera through another window 11, is reflected by another folder mirror 08 to a notch filter 03, and passes the notch filter 03 and a variety of optical components (for example, a VIS-NIR lens 12). The visible light reaches an image sensor (for example, a camera manufactured by Basler Inc., or any other suitable camera) that detects the visible light and generates a sensor signal. The visible light generated sensor signal is transferred from the camera to an image processing unit for generating a visible image frame. (FIG. 6B) Field of illumination for the custom integrated lens and camera solution. In one non-limiting example, the unit may measure 7.75"×3.74"×2.06" and may weight approximately 3.8 lbs allowing it to be attached to commercial endoscope holders. In one non-limiting example, with a focal distance of about 45 cm, it may sit far outside the surgical field and allow instruments and specimen to be easily passed under it during surgical excision. The camera output is connected to an image processing computer and then fed to HD video monitor for display. (FIG. 6C) A scheme of the imaging system. An excitation light for an infrared or near-infrared fluorophore is emitted from a laser, and through the first light-conducting channel, is cleaned up by a laser clean-up filter and reaches a sample labeled with the infrared or near-infrared fluorophore to excite the infrared or near-infrared fluorophore. An emission light is emitted from the excited infrared or near-infrared fluorophore in the sample, and through the third light-conducting channel, passes through a notch filter and reaches an image sensor. A visible light is emitted from a white light source, and through the second light-conducting channel, reaches and illuminates the sample. The visible from the illuminated sample, through the fourth light-conducting channel, reaches the image sensor. The first, second, third and fourth channels may include various optical components including but not limited to optical fibers, optical filters, optical enhancers, optical attenuators, beam splitters, condensers, diffusers, windows, holes, mirrors, shutters, and lens. They may overlap partially or completely; they may be separate channels or combined into one, two, or three channels; and they may include a device such as endoscope and microscope or a portion of the device. The image sensor detects the emission light to generate an infrared light-based sensor signal and detects the visible light to generate a visible light-based sensor signal. The image sensor is connected to an image processing unit and transfers the sensor signals to the image processing unit. The image processing unit processes the sensor signals to generate a composite image frame of infrared light and visible light and transfers the composite image frame to an image displaying unit, which displays a composite image of infrared light and visible light. The imaging system continuously provides a stream of composite images as a real-time video, for example, to assist a surgeon with removing a tumor.

Figure 7:
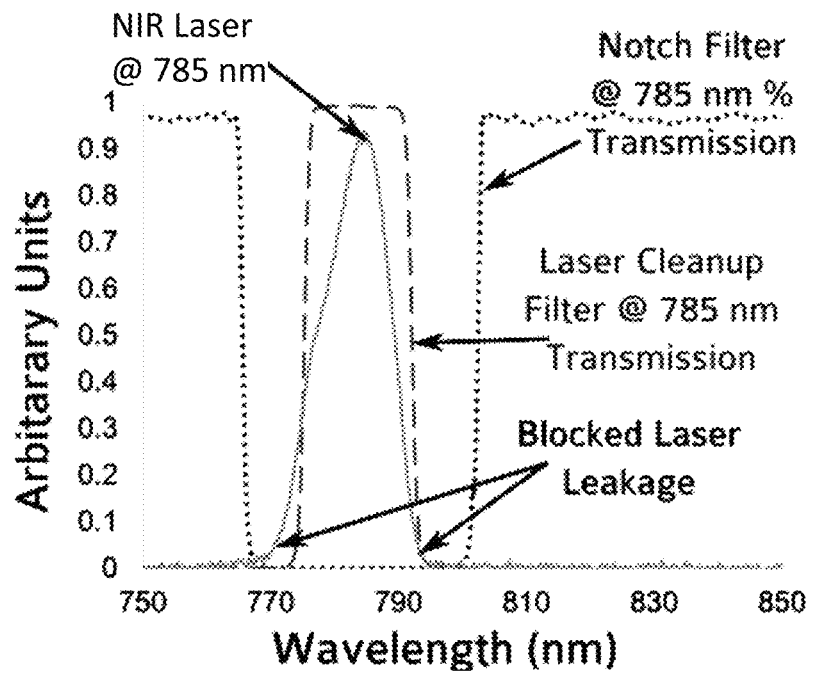

FIG. 7 depicts, in accordance with various embodiments of the present invention, a non-limiting example of filter configuration. The use of very narrow band laser light to excite ICG at the peak absorption wavelength of 785 nm aided by use of a clean-up filter allows for maximum excitation efficiency. In conjunction a notch filter in front of the camera is able to remove the excitation light from the image thus capturing only the fluorescence emission from the target. This configuration allows for imaging fluorescence with maximum efficiency with high SNR.

Figure 8:
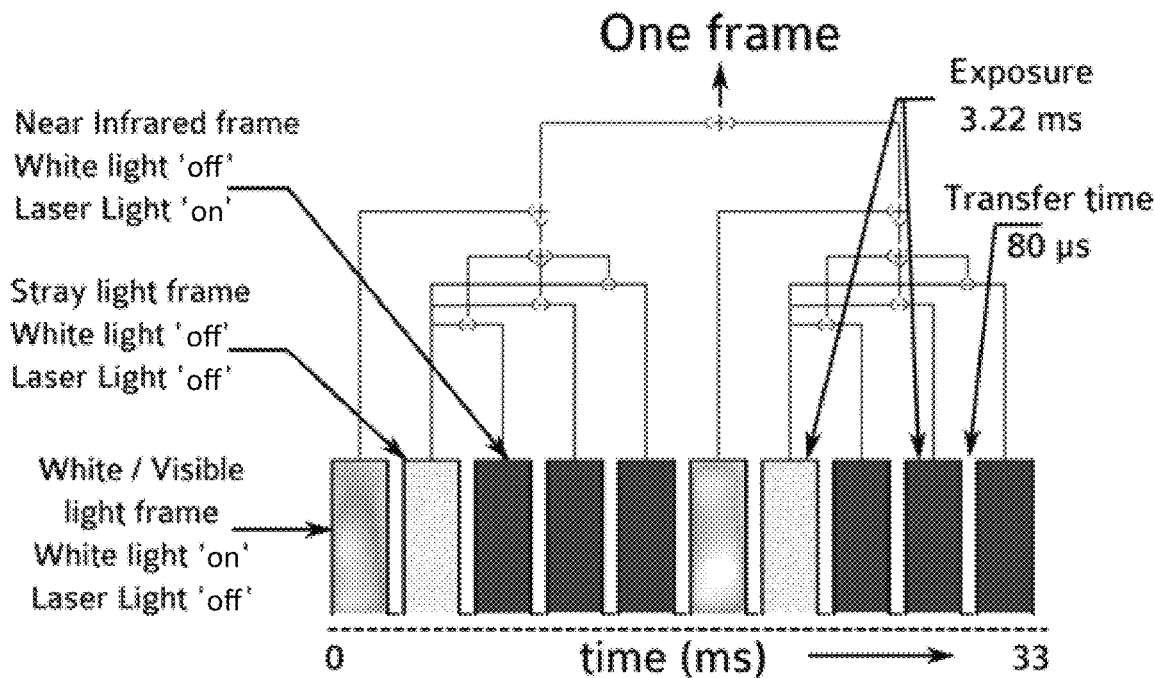

FIG. 8 depicts, in accordance with various embodiments of the present invention, a non-limiting example of timing details of frame capture. This figure shows the timing details of 10 captured frames which are processed to produce a single displayed frame. The camera captures frames at 300 frames per second, while the video display displays 30 frames per second. Each captured frame is synchronized with the white light and NIR laser turning "ON" and "OFF". The visible or natural light frame is captured when the laser is "off" (no fluorescence) and only white light is "ON". When both light sources are "OFF" then SIRIS captures the stray light (background). This background is subtracted from the fluorescence frame when only the laser in "ON" and the white light is "OFF". Dividing this frame capture into groups of 5 frames each reduces the ghosting effect during camera movement.

Figure 9:
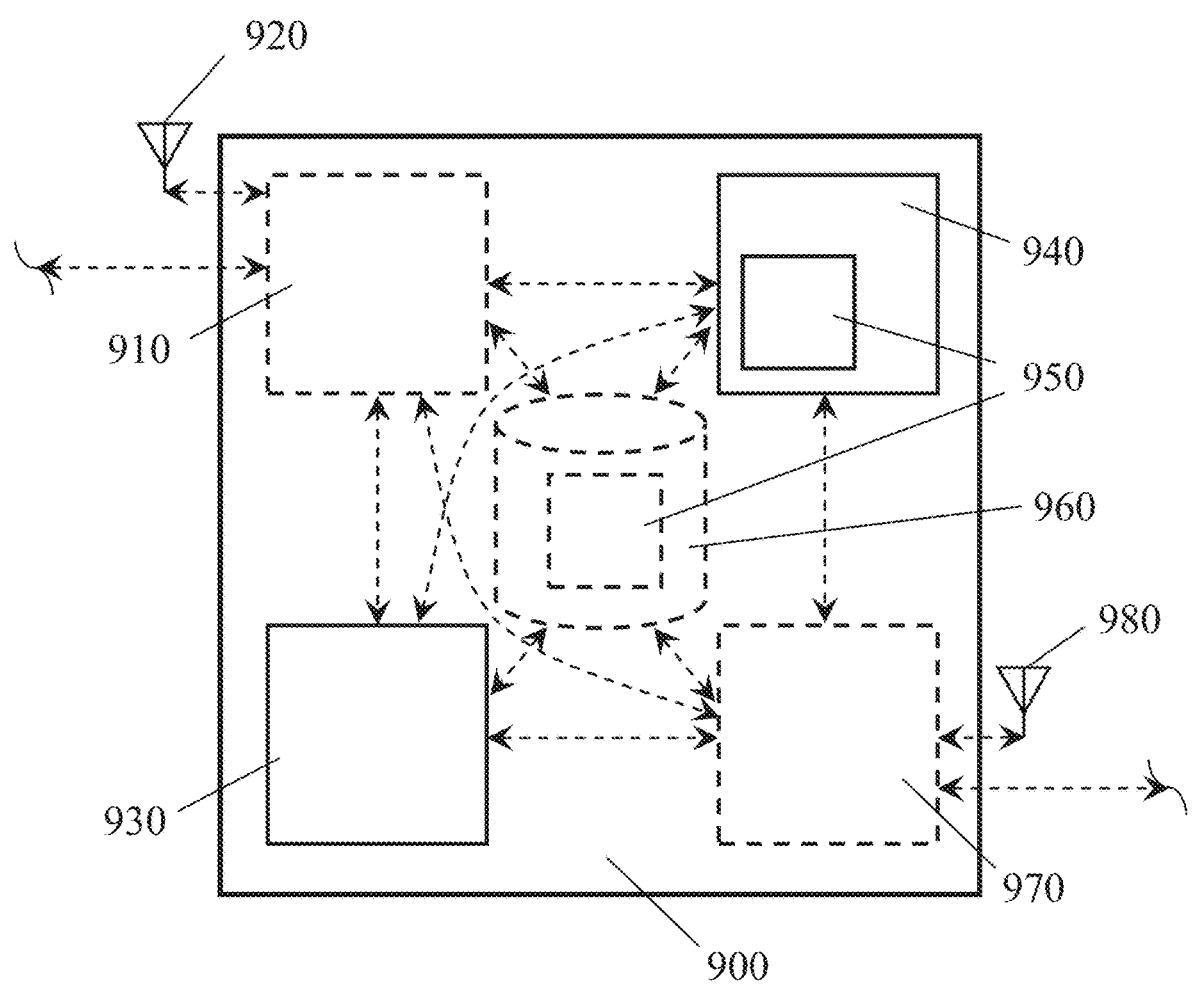

FIG. 9 depicts, in accordance with various embodiments of the present invention, a non-limiting example of a device or a computer system comprising one or more processors and a memory storing one or more programs for execution by the one or more processors.

Figure 10:
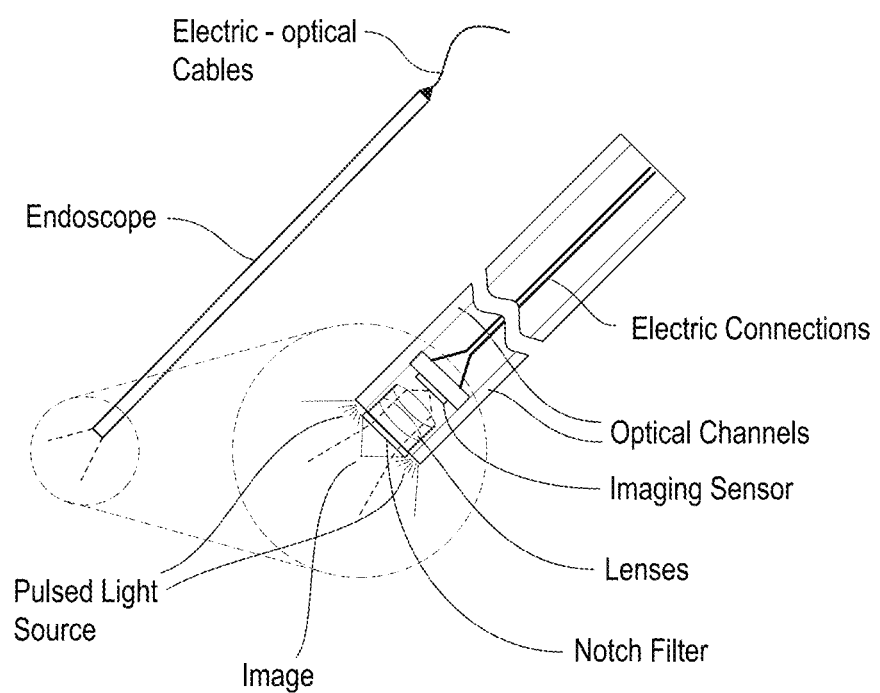

FIG. 10 depicts, in accordance with various embodiments of the present invention, an imaging system for visualizing tumors. In this example, the image sensor is mounted at the patient end of an endoscope.

DETAILED DESCRIPTION OF THE INVENTION

All references cited herein are incorporated by reference in their entirety as though fully set forth. Unless defined otherwise, technical and scientific terms used herein have the same meaning as commonly understood by one of ordinary skill in the art to which this invention belongs. Allen et al., *Remington: The Science and Practice of Pharmacy* 22$^{nd}$ ed., Pharmaceutical Press (Sep. 15, 2012); Hornyak et al., *Introduction to Nanoscience and Nanotechnology*, CRC Press (2008); Singleton and Sainsbury, *Dictionary of Microbiology and Molecular Biology* 3$^{rd}$ ed., revised ed., J. Wiley & Sons (New York, N.Y. 2006); Smith, *March's Advanced Organic Chemistry Reactions, Mechanisms and Structure* 7$^{th}$ ed., J. Wiley & Sons (New York, N.Y. 2013); Singleton, *Dictionary of DNA and Genome Technology* 3$^{rd}$ ed., Wiley-Blackwell (Nov. 28, 2012); and Green and Sambrook, *Molecular Cloning: A Laboratory Manual* 4th ed., Cold Spring Harbor Laboratory Press (Cold Spring Harbor, N.Y. 2012), provide one skilled in the art with a general guide to many of the terms used in the present application. For references on how to prepare antibodies, see Greenfield, Antibodies *A Laboratory Manual* 2$^{nd}$ ed., Cold Spring Harbor Press (Cold Spring Harbor N.Y., 2013); Köhler and Milstein, *Derivation of specific antibody-producing tissue culture and tumor lines by cell fusion*, Eur. J. Immunol. 1976 July, 6(7):511-9; Queen and Selick, Humanized immunoglobulins, U.S. Pat. No. 5,585,089 (1996 December); and Riechmann et al., *Reshaping human antibodies for therapy*, Nature 1988 Mar. 24, 332(6162):323-7.

One skilled in the art will recognize many methods and materials similar or equivalent to those described herein, which could be used in the practice of the present invention. Other features and advantages of the invention will become apparent from the following detailed description, taken in conjunction with the accompanying drawings, which illustrate, by way of example, various features of embodiments of the invention. Indeed, the present invention is in no way limited to the methods and materials described. For convenience, certain terms employed herein, in the specification, examples and appended claims are collected here.

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Unless otherwise defined, all technical and scientific terms used herein have the same meaning as commonly understood by one of ordinary skill in the art to which this invention belongs.

As used herein the term "comprising" or "comprises" is used in reference to compositions, methods, and respective component(s) thereof, that are useful to an embodiment, yet open to the inclusion of unspecified elements, whether useful or not. It will be understood by those within the art that, in general, terms used herein are generally intended as "open" terms (e.g., the term "including" should be interpreted as "including but not limited to," the term "having" should be interpreted as "having at least," the term "includes" should be interpreted as "includes but is not limited to," etc.).

Unless stated otherwise, the terms "a" and "an" and "the" and similar references used in the context of describing a particular embodiment of the application (especially in the context of claims) can be construed to cover both the singular and the plural. The recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (for example, "such as") provided with respect to certain embodiments herein is intended merely to better illuminate the application and does not pose a limitation on the scope of the application otherwise claimed. The abbreviation, "e.g." is derived from the Latin exempli gratia, and is used herein to indicate a non-limiting example. Thus, the abbreviation "e.g." is synonymous with the term "for example." No language in the specification should be construed as indicating any non-claimed element essential to the practice of the application.

As used herein, the terms "treat," "treatment," "treating," or "amelioration" when used in reference to a disease, disorder or medical condition, refer to both therapeutic treatment and prophylactic or preventative measures, wherein the object is to prevent, reverse, alleviate, ameliorate, inhibit, lessen, slow down or stop the progression or severity of a symptom or condition. The term "treating" includes reducing or alleviating at least one adverse effect or symptom of a condition. Treatment is generally "effective" if one or more symptoms or clinical markers are reduced. Alternatively, treatment is "effective" if the progression of a disease, disorder or medical condition is reduced or halted. That is, "treatment" includes not just the improvement of symptoms or markers, but also a cessation or at least slowing of progress or worsening of symptoms that would be expected in the absence of treatment. Also, "treatment" may mean to pursue or obtain beneficial results, or lower the chances of the individual developing the condition even if the treatment is ultimately unsuccessful. Those in need of treatment include those already with the condition as well as those prone to have the condition or those in whom the condition is to be prevented.

"Beneficial results" or "desired results" may include, but are in no way limited to, lessening or alleviating the severity of the disease condition, preventing the disease condition from worsening, curing the disease condition, preventing the disease condition from developing, lowering the chances of a patient developing the disease condition, decreasing morbidity and mortality, and prolonging a patient's life or life expectancy. As non-limiting examples, "beneficial results" or "desired results" may be alleviation of one or more symptom(s), diminishment of extent of the deficit, stabilized (i.e., not worsening) state of tumor, delay or slowing of tumor growth, and amelioration or palliation of symptoms associated with tumor.

"Conditions" and "disease conditions," as used herein may include, but are in no way limited to any form of malignant neoplastic cell proliferative disorders or diseases (e.g., tumor and cancer). In accordance with the present invention, "conditions" and "disease conditions," as used herein include but are not limited to any and all conditions involving a tissue difference, i.e., normal vs. abnormal, due to any and all reasons including but not limited to tumor, injury, trauma, ischemia, infection, inflammation, or autoinflammation. Still in accordance with the present invention, "conditions" and "disease conditions," as used herein include but are not limited to any situation where a tissue of interest (e.g., a cancerous, injured, ischemic, infected, or inflammatory tissue) is different from the surrounding tissue (e.g., healthy tissues) due to physiological or pathological causes. Examples of "conditions" and "disease conditions" include but are not limited to tumors, cancers, traumatic brain injury, spinal cord injury, stroke, cerebral hemorrhage, brain ischemia, ischemic heart diseases, ischemic reperfusion injury, cardiovascular diseases, heart valve stenosis, infectious diseases, microbial infections, viral infection, bacterial infection, fungal infection, and autoimmune diseases.

A "cancer" or "tumor" as used herein refers to an uncontrolled growth of cells which interferes with the normal functioning of the bodily organs and systems, and/or all neoplastic cell growth and proliferation, whether malignant or benign, and all pre-cancerous and cancerous cells and tissues. A subject that has a cancer or a tumor is a subject having objectively measurable cancer cells present in the subject's body. Included in this definition are benign and malignant cancers, as well as dormant tumors or micrometastasis. Cancers which migrate from their original location and seed vital organs can eventually lead to the death of the subject through the functional deterioration of the affected organs. As used herein, the term "invasive" refers to the ability to infiltrate and destroy surrounding tissue. Melanoma is an invasive form of skin tumor. As used herein, the term "carcinoma" refers to a cancer arising from epithelial cells. Examples of cancer include, but are not limited to, nervous system tumor, brain tumor, nerve sheath tumor, breast cancer, colon cancer, carcinoma, lung cancer, hepatocellular cancer, gastric cancer, pancreatic cancer, cervical cancer, ovarian cancer, liver cancer, bladder cancer, cancer of the urinary tract, thyroid cancer, renal cancer, renal cell carcinoma, carcinoma, melanoma, head and neck cancer, brain cancer, and prostate cancer, including but not limited to androgen-dependent prostate cancer and androgen-independent prostate cancer. Examples of brain tumor include, but are not limited to, benign brain tumor, malignant brain tumor, primary brain tumor, secondary brain tumor, metastatic brain tumor, glioma, glioblastoma multiforme (GBM), medulloblastoma, ependymoma, astrocytoma, pilocytic astrocytoma, oligodendroglioma, brainstem glioma, optic nerve glioma, mixed glioma such as oligoastrocytoma, low-grade glioma, high-grade glioma, supratentorial glioma, infratentorial glioma, pontine glioma, meningioma, pituitary adenoma, and nerve sheath tumor. Nervous system tumor or nervous system neoplasm refers to any tumor affecting the nervous system. A nervous system tumor can be a tumor in the central nervous system (CNS), in the peripheral nervous system (PNS), or in both CNS and PNS. Examples of nervous system tumor include but are not limited to brain tumor, nerve sheath tumor, and optic nerve glioma.

As used herein, the term "administering," refers to the placement an agent as disclosed herein into a subject by a method or route which results in at least partial localization of the agents at a desired site. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release.

The term "sample" or "biological sample" as used herein denotes a portion of a biological organism. The sample can be a cell, tissue, organ, or body part. A sample can still be integral of the biological organism. For example, when a surgeon is trying to remove a breast tumor from a patient, the sample refers to the breast tissue labeled with infrared dye and imaged with the imaging system described herein. In this situation, the sample is still part of the patient's body before being removed. A sample can be taken or isolated from the biological organism, e.g., a tumor sample removed from a subject. Exemplary biological samples include, but are not limited to, a biofluid sample; serum; plasma; urine; saliva; a tumor sample; a tumor biopsy and/or tissue sample etc. The term also includes a mixture of the above-mentioned samples. The term "sample" also includes untreated or pretreated (or pre-processed) biological samples. In some embodiments, a sample can comprise one or more cells from the subject. In some embodiments, a sample can be a tumor cell sample, e.g. the sample can comprise cancerous cells, cells from a tumor, and/or a tumor biopsy.

As used herein, a "subject" means a human or animal. Usually the animal is a vertebrate such as a primate, rodent, domestic animal or game animal. Primates include chimpanzees, cynomologous monkeys, spider monkeys, and macaques, e.g., Rhesus. Rodents include mice, rats, woodchucks, ferrets, rabbits and hamsters. Domestic and game animals include cows, horses, pigs, deer, bison, buffalo, feline species, e.g., domestic cat, and canine species, e.g., dog, fox, wolf. The terms, "patient", "individual" and "subject" are used interchangeably herein. In an embodiment, the subject is mammal. The mammal can be a human, non-human primate, mouse, rat, dog, cat, horse, or cow, but are not limited to these examples. In addition, the methods described herein can be used to treat domesticated animals and/or pets.

"Mammal" as used herein refers to any member of the class Mammalia, including, without limitation, humans and nonhuman primates such as chimpanzees and other apes and monkey species; farm animals such as cattle, sheep, pigs, goats and horses; domestic mammals such as dogs and cats; laboratory animals including rodents such as mice, rats and guinea pigs, and the like. The term does not denote a particular age or sex. Thus, adult and newborn subjects, as well as fetuses, whether male or female, are intended to be included within the scope of this term.

A subject can be one who has been previously diagnosed with or identified as suffering from or having a condition in need of treatment (e.g., tumor) or one or more complications related to the condition, and optionally, have already undergone treatment for the condition or the one or more complications related to the condition. Alternatively, a subject can also be one who has not been previously diagnosed as having a condition or one or more complications related to the condition. For example, a subject can be one who exhibits one or more risk factors for a condition or one or more complications related to the condition or a subject who does not exhibit risk factors. A "subject in need" of treatment for a particular condition can be a subject suspected of having that condition, diagnosed as having that condition, already treated or being treated for that condition, not treated for that condition, or at risk of developing that condition.

The term "statistically significant" or "significantly" refers to statistical evidence that there is a difference. It is defined as the probability of making a decision to reject the null hypothesis when the null hypothesis is actually true. The decision is often made using the p-value.

In accordance with the invention, "channel", "light channel", and "optical channel" refer to a channel or pathway that conducts light from one place to another. A "channel" can be an optical fiber, an optical filter, an optical enhancer, an optical attenuator, a beam splitter, a condenser, a diffuser, a collimating lens, a window, a hole, a mirror, a shutter, a lens or a set of lens, or a device including but not limited to endoscope and microscope, or their various combinations.

In accordance with the invention, various infrared or near-infrared fluorophores may be used. Examples of these fluorophores include but are not limited to various infrared or near-infrared fluorescent dyes and quantum dots. They are either alone or attached to a targeting moiety such as a peptide, protein, nanoparticle, nanoconjugate, antibody, and nucleic acid (e.g., DNA and RNA strands) or to any other such biologically specific targeting entity. Near-infrared wavelength is a portion of infrared wavelength and is closest to the radiation detectable by the human eye; and mid- and far-infrared are progressively further from the visible spectrum. As such, near-infrared fluorophores are a subset of infrared fluorophores.

Unless otherwise defined herein, scientific and technical terms used in connection with the present application shall have the meanings that are commonly understood by those of ordinary skill in the art to which this disclosure belongs. It should be understood that this invention is not limited to the particular methodology, protocols, and reagents, etc., described herein and as such can vary. The terminology used herein is for the purpose of describing particular embodiments only, and is not intended to limit the scope of the present invention, which is defined solely by the claims.

Various embodiments of the present invention provide an imaging system for imaging a sample comprising an infrared or near-infrared fluorophore. The imaging system comprises: (1) a laser to emit an excitation light for the infrared or near-infrared fluorophore, wherein the excitation light is conducted to the sample; (2) a laser clean-up filter in the excitation light path from the laser to the sample, wherein the laser clean-up filter narrows the wavelength band of the excitation light to the peak absorption band of the infrared or near-infrared fluorophore, wherein the narrowed excitation light excites the infrared or near-infrared fluorophore in the sample to emit an emission light, wherein the emission light is conducted to an image sensor, and wherein there is no infrared filter in the emission light path from the sample to the image sensor; (3) a notch filter in the emission light path from the sample to the image sensor, wherein the notch filter blocks the excitation light; and (4) a white light source to emit a light comprising visible light, wherein the visible light is conducted to the sample, wherein the sample reflects the visible light, wherein the reflected visible light is conducted to the image sensor, wherein the image sensor is one image sensor configured to detect both the emission light and the visible light from the sample and configured to generate sensor signals, and wherein the image sensor comprises blue, green and red pixel sensors.

In various embodiments, the emission light from the sample is not Raman scattered light from the sample. In various embodiments, there is no Fabry-Perot etalon, Raman analysis filter wheel, dispersive element, dispersive prism, isosceles prism, diffraction grating, reflection-type diffraction grating, or transmission-type diffraction grating in the emission light path from the sample to the image sensor. In various embodiments, the emission light is not dispersed or filtered for Raman band selection in the emission light path from the sample to the image sensor. In various embodiments, the image sensor is configured not to detect Raman scattered light from the sample.

In various embodiments, the infrared or near-infrared fluorophore is one from the group consisting of: a cyanide-based infrared or near-infrared fluorophore, indocyanine green (ICG), a functional equivalent of ICG, an analog of ICG, a derivative of ICG, a salt of ICG, IR800, Alexa680, cy5.5, a functional equivalent of IR800, a functional equivalent of Alexa680, a functional equivalent of cy5.5, an analog of IR800, an analog of Alexa680, an analog of cy5.5, a derivative of IR800, a derivative of Alexa680, a derivative of cy5.5, a salt of IR800, a salt of Alexa 680 or a salt of cy5.5. In some embodiments, the various infrared or near-infrared fluorophores described herein may be modified to be more or less lipophilic.

In various embodiments, the laser is pulsed. In various embodiments, the white light source is pulsed. In various embodiments, the image sensor is a CCD image sensor. In various embodiments, the image sensor is a CMOS image sensor. In various embodiments, the laser clean-up filter is not a spatial filter. In various embodiments, the blocking range of the notch filter is broader than the transmitting range of the laser clean-up filter.

In various embodiments, the excitation light comprises light having a wavelength of about 785 nm. In various embodiments, the laser clean-up filter selectively transmits light having a wavelength of about 785 nm. In various embodiments, the notch filter selectively blocks light having a wavelength of about 785 nm.

In various embodiments, the imaging system further comprises a notch beam splitter in the light path from the laser to the sample, whereby the excitation light is reflected by the notch beam splitter to the sample. In various embodiments, the imaging system further comprises a notch beam splitter in the light path from the white light source to the sample, whereby the visible light is transmitted to the sample. In various embodiments, the imaging system further comprises a notch beam splitter that reflects light having a wavelength of about 785 nm.

In various embodiments, the imaging system further comprises an image processing unit to process sensor signals to generate image frames, wherein the image processing unit is connected to the image sensor. In various embodiments, the image processing unit process sensor signals to generate at least one white light frame (WLF) when the sample receives only visible light, at least one stray light frame (SLF) when the sample receives neither visible light nor the excitation light, and one or more near infrared frames (NIFs) when the sample receives only excitation light, and wherein the image processing unit subtracts the SLF from each NIF and then adds together all SLF-subtracted NIFs to generate a final NIF. In various embodiments, the image processing unit false colors the final NIF. In various embodiments, the image processing unit adds the false colored final NIF to the WLF to generate a composite image frame of visible light and infrared light.

In various embodiments, the imaging system further comprises an image displaying unit to display images based on the image frames generated from the image processing unit, wherein the image displaying unit is connected to the image processing unit.

In various embodiments, the excitation light from the laser is conducted to the sample through a first channel, wherein the visible light from the white light source is conducted to the sample through a second channel, wherein the emission light emitted from the sample is conducted to the image sensor through a third channel, and wherein the visible light reflected from the sample is conducted to the image sensor through a fourth channel.

In various embodiments, the excitation light from the laser is conducted to the sample through a first light channel housed in an endoscope, the visible light from the white light source is conducted to the sample through a second light channel housed in the endoscope; and the image sensor is housed in the endoscope at or near the patient end of the endoscope. In some embodiments, the first light channel and the second light channel are one light channel. In other embodiments, the first light channel and the second light channel are two separate light channels. In various embodiments, the first light channel is an optical cable. In various embodiments, the second light channel is an optical cable. In various embodiments, the imaging system further comprises one or more lenses in the emission light path and/or the visible light path from the sample to the image sensor, wherein the one or more lenses are located at or near the patient end of the endoscope.

Various embodiments of the present invention provide a method for imaging a sample comprising an infrared or near-infrared fluorophore. The method comprises: (1) operating a laser to emit an excitation light for the infrared or near-infrared fluorophore; (2) conducting the excitation light to the sample; (3) operating a laser clean-up filter in the excitation light path from the laser to the sample to narrow the wavelength band of the excitation light to the peak absorption band of the infrared or near-infrared fluorophore, wherein the narrowed excitation light excites the infrared or near-infrared fluorophore in the sample to emit an emission light; (4) conducting the emission light to an image sensor, wherein there is no infrared filter in the emission light path from the sample to the image sensor; (5) operating a notch filter in the emission light path from the sample to the image sensor to block the excitation light; (6) operating a white light source to emit a light comprising visible light; (7) conducting the visible light to the sample, wherein the sample reflects the visible light; (8) conducting the reflected visible light to the image sensor; and (9) operating the image sensor to detect both the emission light and the visible light from the sample and to generate sensor signals, wherein the image sensor is one image sensor and comprises blue, green and red pixel sensors.

In various embodiments, the emission light from the sample is not Raman scattered light from the sample. In various embodiments, the method does not include a step of operating Fabry-Perot etalon, Raman analysis filter wheel, dispersive element, dispersive prism, isosceles prism, diffraction grating, reflection-type diffraction grating, or transmission-type diffraction grating in the emission light path from the sample to the image sensor. In various embodiments, the method does not include a step of dispersing the emission light in the emission light path from the sample to the image sensor. In various embodiments, the method does not include a step of filtering the emission light for Raman band selection in the emission light path from the sample to the image sensor. In various embodiments, the method does not include a step of detecting Raman scatter light from the sample.

In various embodiments, the method further comprises performing a surgery on a subject to access the sample or to isolate the sample. In various embodiments, the method further comprises labeling the sample with an infrared or near-infrared fluorophore.

In various embodiments, the present invention provides an imaging system for imaging a sample. In accordance with the invention, the sample comprises an infrared or near-infrared fluorophore. The imaging system comprises: an image sensor, a laser, a laser clean-up filter, a notch filter, and a white light source. The image sensor detects visible light and infrared light and to generate sensor signals. The laser emits an excitation light for the infrared or near-infrared fluorophore. The laser clean-up filter is placed in the light path from the laser to the sample, and narrows the wavelength band of the excitation light to the peak absorption band of the infrared or near-infrared fluorophore. The narrowed excitation light excites the infrared or near-infrared fluorophore in the sample to emit an emission light. The notch filter is placed in the light path from the sample to the image sensor, and blocks the excitation light. The white light source emits a light comprising visible light. In accordance with the invention, visible light can have a spectrum of 400-700 nm. In various embodiments, the imaging system further comprises a fast trigger unit.

In some embodiments, there is an infrared filter in the light path from the white light source to the sample. In various embodiments, the intensity of the laser is controlled to ensure uniform excitation on the same area illuminated by visible light. Although lasers by definition are monochromatic, which mean they do not have a broad band range, in practice most lasers will have a small amount of emission in the adjacent color bands. In various embodiments, the laser is a narrow band laser including but not limited to a laser having a wavelength range that spans no more than 5, 10, 15, or 20 nm. As a non-limiting example, the laser can emit light having about 775-795 nm wavelength with a peak at about 785 nm (FIG. 7).

In various embodiments, the blocking range of the notch filter is broader than the transmitting range of the laser clean-up filter. In various embodiments, the blocking range of the notch filter is about 5-10 nm, 10-15 nm, or 15-20 nm broader than the transmitting range of the laser clean-up filter. In various embodiments, the blocking range of the notch filter is about 5-10%, 10-15%, 15-20%, 20-25%, 25-30%, 30-40%, 40-50%, 50-100% or 100-200% broader than the transmitting range of the laser clean-up filter. As a non-limiting example, the transmitting range of the laser clean-up filter can be about 775-795 nm and the blocking range of the notch filter can be about 770-800 nm, 765-805 nm, or 760-810 nm.

In various embodiments, the excitation light comprises light having a wavelength of about 785 nm. In various embodiments, the laser clean-up filter selectively transmits light having a wavelength of about 785 nm. In various embodiments, the notch filter selectively blocks light having a wavelength of about 785 nm.

In various embodiments, the imaging system further comprises a notch beam splitter in the light path from the laser to the sample, whereby the excitation light is reflected by the notch beam splitter to the sample. In various embodiments, the imaging system further comprises a notch beam splitter in the light path from the white light source to the sample, whereby the visible light is transmitted to the sample. The notch beam splitter in the light path from the laser to the sample and the notch beam splitter in the light path from the white light source to the sample can be one single notch beam splitter or two separate notch beam splitters. In one embodiment, the notch beam splitter can split light at a wavelength of about 700, 725 or 750 nm. In another embodiment, the notch beam splitter that reflects light having a wavelength of about 785 nm.

In various embodiments, there is no infrared filter in the light path from the sample to the image sensor. In various embodiments, there is no infrared filter in the light path from the laser to the sample. In some embodiments, there is an optical filter to block the excitation light in the light path from the sample to the image sensor. In other embodiments, there is no optical filter to block the excitation light in the light path from the laser to the sample.

In various embodiments, the imaging system further comprises an image processing unit to process sensor signals to generate image frames. In accordance with the present invention, the image processing unit is connected to the image sensor. In various embodiments, the image processing unit process sensor signals to generate at least one white light frame (WLF) when the sample receives only visible light, at least one stray light frame (SLF) when the sample receives neither visible light nor the excitation light, and one or more near infrared frames (NIFs) when the sample receives only excitation light, and wherein the image processing unit subtracts the SLF from each NIF and then adds together all SLF-subtracted NIFs to generate a final NIF. In various embodiments, the image processing unit false colors the final NIF. In various embodiments, the image processing unit adds the false colored final NIF to the WLF to generate a composite image frame of visible light and infrared light. In various embodiments, the image processing unit generates composite image frames of visible light and infrared light at a frequency of 30 Hz.

In various embodiments, during one cycle of generating one composite image frame of visible light and infrared light, the imaging system generates one or more WLFs, one or more SLFs, and one or more NIFs. In accordance with the present invention, the sequence of WLF (W), SLF (S) and NIF (N) during one cycle has many suitable choices, including but not limited to, W-S-N, W-N-S, S-W-N, S-N-W, N-S-W, and N-W-S. Still in accordance with the present invention, the numbers of WLF (W), SLF (S) and NIF (N) during one cycle has many suitable choices, including but not limited to, 1 W-1S-1N, 1 W-1S-2N, 1 W-1S-3N, 2 W-2S-6N, and 1 W-1S-3N-1 W-1S-3N. In various embodiments, the imaging system continuously repeats a cycle to generate a continuous stream of composite image frames as a real-time video.

In various embodiments, the imaging system further comprises an image displaying unit to display images based on the image frames generated from the image processing unit. In accordance with the present invention, the image displaying unit is connected to the image processing unit. Examples of the image displaying unit include but are not limited to monitors, projectors, phones, tablets, and screens. In some embodiments, the image displaying unit displays composite image frames of visible light and infrared light at a frequency of 30 Hz.

In various embodiments, the imaging system further comprises a first channel to conduct the excitation light from the laser to the sample, a second channel to conduct the visible light from the white light source to the sample, a third channel to conduct the emission light from the sample to the image sensor, and a fourth channel to conduct the visible light from the sample to the image sensor. In accordance with the present invention, the first, second, third and fourth channels are four separate channels or combined into one, two, or three channels. Still in accordance with the present invention, two or more of the four channels may overlap partially or completely on their light paths. In various embodiments, the first, second, third and fourth channels are endoscope or microscope.

In various embodiments, the present invention provides an imaging system for imaging a sample. In accordance with the invention, the sample comprises an infrared or near-infrared fluorophore. As a non-limiting example, the infrared or near-infrared fluorophore can be a cyanide-based infrared or near-infrared fluorophore (e.g., indocyanine green (ICG)). The system comprises: (a) an image sensor, (b) a laser, (c) a laser clean-up filter, (d) a first channel, (e) a white light source, (f) a second channel, (g) a notch beam splitter, (h) a third channel, (i) a fourth channel, (j) a notch filter, (k) an image processing unit, and (l) an image displaying unit. (a) The image sensor detects visible light and infrared light and generates sensor signals at a first frequency. There is no infrared filter in the light path from the sample to the image sensor. The image sensor comprises blue, green and red pixel sensors. Examples of the image sensor include but are not limited to CCD image sensors and CMOS image sensors. (b) The laser emits an excitation light for the infrared or near-infrared fluorophore. (c) The laser clean-up filter is placed in the light path from the laser to the sample. The laser clean-up filter narrows the wavelength band of the excitation light to the peak absorption band of the infrared or near-infrared fluorophore, and the narrowed excitation light excites the infrared or near-infrared fluorophore in the sample to emit an emission light. (d) The first channel conducts the excitation light from the laser to the sample. (e) The white light source emits a light comprising visible light. (f) The second channel conducts the visible light from the white light source to the sample. (g) The notch beam splitter is placed in the light path from the laser to the sample and in the light path from the white light source to the sample. The excitation light is reflected by the notch beam splitter to the sample and the visible light is transmitted through the notch beam splitter to the sample. (h) The third channel conducts the emission light from the sample to the image sensor. (i) The fourth channel conducts the visible light from the sample to the image sensor. (j) The notch filter is placed in the light path from the sample to the image sensor, and the notch filter blocks the excitation light. (k) The image processing unit is connected to the image sensor and processes sensor signals to generate image frames. At least one white light frame (WLF) is generated when the sample receives only visible light, at least one stray light frame (SLF) is generated when the sample receives neither visible light nor the excitation light, and one or more near infrared frames (NIFs) are generated when the sample receives only excitation light. The image processing unit subtracts the SLF from each NIF and then adds together all SLF-subtracted NIFs to generate a final NIF. The image processing unit false colors the final NIF and adds the false colored final NIF to the WLF to generate a composite image frame of visible light and infrared light. (l) The image displaying unit is connected to the image processing unit and displays images based on the image frames generated from the image processing unit.

In various embodiments, the present invention provides an imaging system for imaging a sample. In accordance with the invention, the sample comprises an infrared or near-infrared fluorophore. As a non-limiting example, the infrared or near-infrared fluorophore can be a cyanide-based infrared or near-infrared fluorophore (e.g., indocyanine green (ICG)). The system comprises: (a) a laser; (b) a white light source; (c) an endoscope comprising a first light channel, a second light channel, an image sensor and a notch filter; (d) an image processing unit; and (e) an image displaying unit. (a) The laser emits an excitation light for the infrared or near-infrared fluorophore. (b) The white light source emits a light comprising visible light. (c) The first light channel conducts the excitation light from the laser to the sample; the second channel conducts the visible light from the white light source to the sample; the image sensor is located at or near the patient end of the endoscope, and detects visible light and infrared light and generates sensor signals; and the notch filter is located at or near the patient end of the endoscope, is in the light path from the sample to the image sensor, and blocks the excitation light. (d) The image processing unit is connected to the image sensor, and processes sensor signals to generate image frames. (e) The image displaying unit is connected to the image processing unit, and displays images based on the image frames generated form the image processing unit. In some embodiments, the laser is pulsed. In some embodiments, the white light source is pulsed. In some embodiments, the first light channel is an optical cable. In some embodiments, the second light channel is an optical cable. In some embodiments, the image processing unit is connected to the image sensor through an electrical cable. In various embodiments, the imaging system further comprises one or more lenses in the light path from the sample to the image sensor, wherein the one or more lenses are located at or near the patient end of the endoscope.

In various embodiments, the image sensor comprises blue, green and red pixel sensors. In one embodiment, all the blue, green and red pixel sensors are sensitive to both visible light and infrared light. In various embodiments, the image sensor is a CCD image sensor that detects visible light and infrared light and generates CCD image signals. In various embodiments, the image sensor is a CMOS image sensor that detects visible light and infrared light and generates CMOS image signals. In various embodiments, the image sensor is without a NIR long pass filter.

In various embodiments, the imaging system further comprises software that controls all the components of the imaging system. FIG. 9 depicts a device or a computer system 900 comprising one or more processors 930 and a memory 940 storing one or more programs 950 for execution by the one or more processors 930.

In some embodiments, the device or computer system 900 can further comprise a non-transitory computer-readable storage medium 960 storing the one or more programs 950 for execution by the one or more processors 930 of the device or computer system 900.

In some embodiments, the device or computer system 900 can further comprise one or more input devices 910, which can be configured to send or receive information to or from any one from the group consisting of: an external device (not shown), the one or more processors 930, the memory 940, the non-transitory computer-readable storage medium 960, and one or more output devices 970. The one or more input devices 910 can be configured to wirelessly send or receive information to or from the external device via a means for wireless communication, such as an antenna 920, a transceiver (not shown) or the like.

In some embodiments, the device or computer system 900 can further comprise one or more output devices 970, which can be configured to send or receive information to or from any one from the group consisting of: an external device (not shown), the one or more input devices 910, the one or more processors 930, the memory 940, and the non-transitory computer-readable storage medium 960. The one or more output devices 970 can be configured to wirelessly send or receive information to or from the external device via a means for wireless communication, such as an antenna 980, a transceiver (not shown) or the like.

Each of the above identified modules or programs correspond to a set of instructions for performing a function described above. These modules and programs (i.e., sets of instructions) need not be implemented as separate software programs, procedures or modules, and thus various subsets of these modules may be combined or otherwise re-arranged in various embodiments. In some embodiments, memory may store a subset of the modules and data structures identified above. Furthermore, memory may store additional modules and data structures not described above.

The illustrated aspects of the disclosure may also be practiced in distributed computing environments where certain tasks are performed by remote processing devices that are linked through a communications network. In a distributed computing environment, program modules can be located in both local and remote memory storage devices.

Moreover, it is to be appreciated that various components described herein can include electrical circuit(s) that can include components and circuitry elements of suitable value in order to implement the embodiments of the subject innovation(s). Furthermore, it can be appreciated that many of the various components can be implemented on one or more integrated circuit (IC) chips. For example, in one embodiment, a set of components can be implemented in a single IC chip. In other embodiments, one or more of respective components are fabricated or implemented on separate IC chips.

What has been described above includes examples of the embodiments of the present invention. It is, of course, not possible to describe every conceivable combination of components or methodologies for purposes of describing the claimed subject matter, but it is to be appreciated that many further combinations and permutations of the subject innovation are possible. Accordingly, the claimed subject matter is intended to embrace all such alterations, modifications, and variations that fall within the spirit and scope of the appended claims. Moreover, the above description of illustrated embodiments of the subject disclosure, including what is described in the Abstract, is not intended to be exhaustive or to limit the disclosed embodiments to the precise forms disclosed. While specific embodiments and examples are described herein for illustrative purposes, various modifications are possible that are considered within the scope of such embodiments and examples, as those skilled in the relevant art can recognize.

In particular and in regard to the various functions performed by the above described components, devices, circuits, systems and the like, the terms used to describe such components are intended to correspond, unless otherwise indicated, to any component which performs the specified function of the described component (e.g., a functional equivalent), even though not structurally equivalent to the disclosed structure, which performs the function in the herein illustrated exemplary aspects of the claimed subject matter. In this regard, it will also be recognized that the innovation includes a system as well as a computer-readable storage medium having computer-executable instructions for performing the acts and/or events of the various methods of the claimed subject matter.

The aforementioned systems/circuits/modules have been described with respect to interaction between several components/blocks. It can be appreciated that such systems/circuits and components/blocks can include those components or specified sub-components, some of the specified components or sub-components, and/or additional components, and according to various permutations and combinations of the foregoing. Sub-components can also be implemented as components communicatively coupled to other components rather than included within parent components (hierarchical). Additionally, it should be noted that one or more components may be combined into a single component providing aggregate functionality or divided into several separate sub-components, and any one or more middle layers, such as a management layer, may be provided to communicatively couple to such sub-components in order to provide integrated functionality. Any components described herein may also interact with one or more other components not specifically described herein but known by those of skill in the art.

In addition, while a particular feature of the subject innovation may have been disclosed with respect to only one of several implementations, such feature may be combined with one or more other features of the other implementations as may be desired and advantageous for any given or particular application. Furthermore, to the extent that the terms "includes," "including," "has," "contains," variants thereof, and other similar words are used in either the detailed description or the claims, these terms are intended to be inclusive in a manner similar to the term "comprising" as an open transition word without precluding any additional or other elements.

As used in this application, the terms "component," "module," "system," or the like are generally intended to refer to a computer-related entity, either hardware (e.g., a circuit), a combination of hardware and software, software, or an entity related to an operational machine with one or more specific functionalities. For example, a component may be, but is not limited to being, a process running on a processor (e.g., digital signal processor), a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers. Further, a "device" can come in the form of specially designed hardware; generalized hardware made specialized by the execution of software thereon that enables the hardware to perform specific function; software stored on a computer-readable medium; or a combination thereof.

Moreover, the words "example" or "exemplary" are used herein to mean serving as an example, instance, or illustration. Any aspect or design described herein as "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims should generally be construed to mean "one or more" unless specified otherwise or clear from context to be directed to a singular form.

Computing devices typically include a variety of media, which can include computer-readable storage media and/or communications media, in which these two terms are used herein differently from one another as follows. Computer-readable storage media can be any available storage media that can be accessed by the computer, is typically of a non-transitory nature, and can include both volatile and nonvolatile media, removable and non-removable media. By way of example, and not limitation, computer-readable storage media can be implemented in connection with any method or technology for storage of information such as computer-readable instructions, program modules, structured data, or unstructured data. Computer-readable storage media can include, but are not limited to, RAM, ROM, EEPROM, flash memory or other memory technology, CD-ROM, digital versatile disk (DVD) or other optical disk storage, magnetic cassettes, magnetic tape, magnetic disk storage or other magnetic storage devices, or other tangible and/or non-transitory media which can be used to store desired information. Computer-readable storage media can be accessed by one or more local or remote computing devices, e.g., via access requests, queries or other data retrieval protocols, for a variety of operations with respect to the information stored by the medium.

On the other hand, communications media typically embody computer-readable instructions, data structures, program modules or other structured or unstructured data in a data signal that can be transitory such as a modulated data signal, e.g., a carrier wave or other transport mechanism, and includes any information delivery or transport media. The term "modulated data signal" or signals refers to a signal that has one or more of its characteristics set or changed in such a manner as to encode information in one or more signals. By way of example, and not limitation, communication media include wired media, such as a wired network or direct-wired connection, and wireless media such as acoustic, RF, infrared and other wireless media.

In view of the exemplary systems described above, methodologies that may be implemented in accordance with the described subject matter will be better appreciated with reference to the flowcharts of the various figures. For simplicity of explanation, the methodologies are depicted and described as a series of acts. However, acts in accordance with this disclosure can occur in various orders and/or concurrently, and with other acts not presented and described herein. Furthermore, not all illustrated acts may be required to implement the methodologies in accordance with the disclosed subject matter. In addition, those skilled in the art will understand and appreciate that the methodologies could alternatively be represented as a series of interrelated states via a state diagram or events. Additionally, it should be appreciated that the methodologies disclosed in this specification are capable of being stored on an article of manufacture to facilitate transporting and transferring such methodologies to computing devices. The term article of manufacture, as used herein, is intended to encompass a computer program accessible from any computer-readable device or storage media.

In various embodiments, the present invention provides a computer implemented method for imaging a sample comprising an infrared or near-infrared fluorophore, comprising: on a device having one or more processors and a memory storing one or more programs for execution by the one or more processors, the one or more programs including instructions for: operating an image sensor to detect visible light and infrared light and generating sensor signals; operating a laser to emit an excitation light for the infrared or near-infrared fluorophore; operating a laser clean-up filter in the light path from the laser to the sample, whereby the laser clean-up filter narrows the wavelength band of the excitation light to the peak absorption band of the infrared or near-infrared fluorophore, and whereby the narrowed excitation light excites the infrared or near-infrared fluorophore in the sample to emit an emission light; operating a notch filter in the light path from the sample to the image sensor, whereby the notch filter blocks the excitation light; and operating a white light source to emit a light comprising visible light.

In various embodiments, the present invention provides a computer system for imaging a sample comprising an infrared or near-infrared fluorophore, comprising: one or more processors and memory to store one or more programs, the one or more programs comprising instructions for: operating an image sensor to detect visible light and infrared light and generating sensor signals; operating a laser to emit an excitation light for the infrared or near-infrared fluorophore; operating a laser clean-up filter in the light path from the laser to the sample, whereby the laser clean-up filter narrows the wavelength band of the excitation light to the peak absorption band of the infrared or near-infrared fluorophore, and whereby the narrowed excitation light excites the infrared or near-infrared fluorophore in the sample to emit an emission light; operating a notch filter in the light path from the sample to the image sensor, whereby the notch filter blocks the excitation light; and operating a white light source to emit a light comprising visible light.

In various embodiments, the present invention provides a non-transitory computer-readable storage medium storing one or more programs for imaging a sample comprising an infrared or near-infrared fluorophore, the one or more programs for execution by one or more processors of a computer system, the one or more programs comprising instructions for: operating an image sensor to detect visible light and infrared light and generating sensor signals; operating a laser to emit an excitation light for the infrared or near-infrared fluorophore; operating a laser clean-up filter in the light path from the laser to the sample, whereby the laser clean-up filter narrows the wavelength band of the excitation light to the peak absorption band of the infrared or near-infrared fluorophore, and whereby the narrowed excitation light excites the infrared or near-infrared fluorophore in the sample to emit an emission light; operating a notch filter in the light path from the sample to the image sensor, whereby the notch filter blocks the excitation light; and operating a white light source to emit a light comprising visible light.

In various embodiments, the present invention provides a computer implemented method for imaging a sample comprising an infrared or near-infrared fluorophore, comprising: on a device having one or more processors and a memory storing one or more programs for execution by the one or more processors, the one or more programs including instructions for: (a) operating an image sensor to detect visible light and infrared light and generate sensor signals, wherein there is no infrared filter in the light path from the sample to the image sensor, and wherein the image sensor comprises blue, green and red pixel sensors; (b) operating a laser to emit an excitation light for the infrared or near-infrared fluorophore; (c) operating a laser clean-up filter in the light path from the laser to the sample, whereby the laser clean-up filter narrows the wavelength band of the excitation light to the peak absorption band of the infrared or near-infrared fluorophore, and whereby the narrowed excitation light excites the infrared or near-infrared fluorophore in the sample to emit an emission light; (d) operating a first channel to conduct the excitation light from the laser to the sample; (e) operating a white light source to emit a light comprising visible light; (f) operating a second channel to conduct the visible light from the white light source to the sample; (g) operating a notch beam splitter in the light path from the laser to the sample and in the light path from the white light source to the sample, whereby the excitation light is reflected by the notch beam splitter to the sample and the visible light is transmitted through the notch beam splitter to the sample; (h) operating a third channel to conduct the emission light from the sample to the image sensor; (i) operating a fourth channel to conduct the visible light from the sample to the image sensor; (j) operating a notch filter in the light path from the sample to the image sensor, whereby the notch filter blocks the excitation light; and (k) operating an image processing unit to process sensor signals to generate image frames, wherein the image processing unit is connected to the image sensor, wherein at least one white light frame (WLF) is generated when the sample receives only visible light, wherein at least one stray light frame (SLF) is generated when the sample receives neither visible light nor the excitation light, wherein one or more near infrared frames (NIFs) are generated when the sample receives only excitation light, wherein the image processing unit subtracts the SLF from each NIF and then adds together all SLF-subtracted NIFs to generate a final NIF, wherein the image processing unit false colors the final NIF, and wherein the image processing unit adds the false colored final NIF to the WLF to generate a composite image frame of visible light and infrared light. (l) operating an image displaying unit to display images based on the image frames generated from the image processing unit, wherein the image displaying unit is connected to the image processing unit.

In various embodiments, the present invention provides a computer system for imaging a sample comprising an infrared or near-infrared fluorophore, comprising: one or more processors and memory to store one or more programs, the one or more programs comprising instructions for: (a) operating an image sensor to detect visible light and infrared light and generate sensor signals, wherein there is no infrared filter in the light path from the sample to the image sensor, and wherein the image sensor comprises blue, green and red pixel sensors; (b) operating a laser to emit an excitation light for the infrared or near-infrared fluorophore; (c) operating a laser clean-up filter in the light path from the laser to the sample, whereby the laser clean-up filter narrows the wavelength band of the excitation light to the peak absorption band of the infrared or near-infrared fluorophore, and whereby the narrowed excitation light excites the infrared or near-infrared fluorophore in the sample to emit an emission light; (d) operating a first channel to conduct the excitation light from the laser to the sample; (e) operating a white light source to emit a light comprising visible light; (f) operating a second channel to conduct the visible light from the white light source to the sample; (g) operating a notch beam splitter in the light path from the laser to the sample and in the light path from the white light source to the sample, whereby the excitation light is reflected by the notch beam splitter to the sample and the visible light is transmitted through the notch beam splitter to the sample; (h) operating a third channel to conduct the emission light from the sample to the image sensor; (i) operating a fourth channel to conduct the visible light from the sample to the image sensor; (j) operating a notch filter in the light path from the sample to the image sensor, whereby the notch filter blocks the excitation light; (k) operating an image processing unit to process sensor signals to generate image frames, wherein the image processing unit is connected to the image sensor, wherein at least one white light frame (WLF) is generated when the sample receives only visible light, wherein at least one stray light frame (SLF) is generated when the sample receives neither visible light nor the excitation light, wherein one or more near infrared frames (NIFs) are generated when the sample receives only excitation light, wherein the image processing unit subtracts the SLF from each NIF and then adds together all SLF-subtracted NIFs to generate a final NIF, wherein the image processing unit false colors the final NIF, and wherein the image processing unit adds the false colored final NIF to the WLF to generate a composite image frame of visible light and infrared light; and (l) operating an image displaying unit to display images based on the image frames generated from the image processing unit, wherein the image displaying unit is connected to the image processing unit.

In various embodiments, the present invention provides a non-transitory computer-readable storage medium storing one or more programs for imaging a sample comprising an infrared or near-infrared fluorophore, the one or more programs for execution by one or more processors of a computer system, the one or more programs comprising instructions for: (a) operating an image sensor to detect visible light and infrared light and generate sensor signals, wherein there is no infrared filter in the light path from the sample to the image sensor, and wherein the image sensor comprises blue, green and red pixel sensors; (b) operating a laser to emit an excitation light for the infrared or near-infrared fluorophore; (c) operating a laser clean-up filter in the light path from the laser to the sample, whereby the laser clean-up filter narrows the wavelength band of the excitation light to the peak absorption band of the infrared or near-infrared fluorophore, and whereby the narrowed excitation light excites the infrared or near-infrared fluorophore in the sample to emit an emission light; (d) operating a first channel to conduct the excitation light from the laser to the sample; (e) operating a white light source to emit a light comprising visible light; (f) operating a second channel to conduct the visible light from the white light source to the sample; (g) operating a notch beam splitter in the light path from the laser to the sample and in the light path from the white light source to the sample, whereby the excitation light is reflected by the notch beam splitter to the sample and the visible light is transmitted through the notch beam splitter to the sample; (h) operating a third channel to conduct the emission light from the sample to the image sensor; (i) operating a fourth channel to conduct the visible light from the sample to the image sensor; (j) operating a notch filter in the light path from the sample to the image sensor, whereby the notch filter blocks the excitation light; (k) operating an image processing unit to process sensor signals to generate image frames, wherein the image processing unit is connected to the image sensor, wherein at least one white light frame (WLF) is generated when the sample receives only visible light, wherein at least one stray light frame (SLF) is generated when the sample receives neither visible light nor the excitation light, wherein one or more near infrared frames (NIFs) are generated when the sample receives only excitation light, wherein the image processing unit subtracts the SLF from each NIF and then adds together all SLF-subtracted NIFs to generate a final NIF, wherein the image processing unit false colors the final NIF, and wherein the image processing unit adds the false colored final NIF to the WLF to generate a composite image frame of visible light and infrared light; and (l) operating an image displaying unit to display images based on the image frames generated from the image processing unit, wherein the image displaying unit is connected to the image processing unit.

In various embodiments, the present invention provides a computer implemented method for imaging a sample comprising an infrared or near-infrared fluorophore, comprising: on a device having one or more processors and a memory storing one or more programs for execution by the one or more processors, the one or more programs including instructions for: operating an image sensor to detect visible light and infrared light and generate sensor signals; operating a laser to emit an excitation light for the infrared or near-infrared fluorophore and alternate between on and off statuses; operating a notch beam splitter in the light path from the laser to the sample and in the light path from the sample to the image sensor, whereby the excitation light is reflected by the notch beam splitter to the sample, whereby the excitation light excites the infrared or near-infrared fluorophore in the sample to emit an emission light, and whereby the emission light is transmitted through the notch beam splitter to the image sensor; operating a notch filter in the light path from the sample to the image sensor, whereby the notch filter blocks the excitation light; and operating a synchronization module to synchronize the image sensor with the laser and visible light, whereby a single sensor signal is synchronized to a single on or off status of the laser.

In various embodiments, the present invention provides a computer system for imaging a sample comprising an infrared or near-infrared fluorophore, comprising: one or more processors and memory to store one or more programs, the one or more programs comprising instructions for: operating an image sensor to detect visible light and infrared light and generate sensor signals; operating a laser to emit an excitation light for the infrared or near-infrared fluorophore and alternate between on and off statuses; operating a notch beam splitter in the light path from the laser to the sample and in the light path from the sample to the image sensor, whereby the excitation light is reflected by the notch beam splitter to the sample, whereby the excitation light excites the infrared or near-infrared fluorophore in the sample to emit an emission light, and whereby the emission light is transmitted through the notch beam splitter to the image sensor; operating a notch filter in the light path from the sample to the image sensor, whereby the notch filter blocks the excitation light; and operating a synchronization module to synchronize the image sensor with the laser and visible light, whereby a single sensor signal is synchronized to a single on or off status of the laser.

In various embodiments, the present invention provides a non-transitory computer-readable storage medium storing one or more programs for imaging a sample comprising an infrared or near-infrared fluorophore, the one or more programs for execution by one or more processors of a computer system, the one or more programs comprising instructions for: operating an image sensor to detect visible light and infrared light and generate sensor signals; operating a laser to emit an excitation light for the infrared or near-infrared fluorophore and alternate between on and off statuses; operating a notch beam splitter in the light path from the laser to the sample and in the light path from the sample to the image sensor, whereby the excitation light is reflected by the notch beam splitter to the sample, whereby the excitation light excites the infrared or near-infrared fluorophore in the sample to emit an emission light, and whereby the emission light is transmitted through the notch beam splitter to the image sensor; operating a notch filter in the light path from the sample to the image sensor, whereby the notch filter blocks the excitation light; and operating a synchronization module to synchronize the image sensor with the laser and visible light, whereby a single sensor signal is synchronized to a single on or off status of the laser.

In various embodiments, the present invention provides a computer implemented method for imaging a sample comprising an infrared or near-infrared fluorophore, comprising: on a device having one or more processors and a memory storing one or more programs for execution by the one or more processors, the one or more programs including instructions for: (a) operating an image sensor to detect visible light and infrared light and generate sensor signals at a first frequency, wherein there is no infrared filter in the light path from the sample to the image sensor, and wherein the image sensor comprises blue, green and red pixel sensors; (b) operating a laser to emit an excitation light for the infrared or near-infrared fluorophore and to alternate between on and off statuses at a second frequency, wherein the second frequency is half of the first frequency; (c) operating a first channel to conduct the excitation light from the laser to the sample; (d) operating a light source to emit a light comprising visible light; (e) operating a second channel to conduct the visible light from the light source to the sample; (f) operating a notch beam splitter in the light path from the laser to the sample and in the light path from the sample to the image sensor, whereby the excitation light is reflected by the notch beam splitter to the sample, whereby the excitation light excites the infrared or near-infrared fluorophore in the sample to emit an emission light, and whereby the emission light is transmitted through the notch beam splitter to the image sensor; (g) operating a third channel to conduct the emission light from the sample to the image sensor; (h) operating a fourth channel to conduct the visible light from the sample to the image sensor; (i) operating a notch filter in the light path from the sample to the image sensor, whereby the notch filter blocks the excitation light; (j) operating a synchronization module to synchronize the image sensor with the laser and visible light, whereby a single sensor signal is synchronized to a single on or off status of the laser; (k) operating an image processing unit to process sensor signals to generate image frames, wherein the image processing unit is connected to the image sensor, wherein the image processing unit subtracts an image frame generated when the laser is off from the previous or next image frame generated when the laser is on, whereby an infrared-only image frame is generated upon the difference between the two successive image frames, wherein the image processing unit false colors the infrared-only image frame, wherein the image processing unit adds the false colored infrared-only image frame back to the image frame generated when the laser is off, whereby a composite image frame of visible light and infrared light is generated; and (1) operating an image displaying unit to display images based on the image frames generated from the image processing unit, wherein the image displaying unit is connected to the image processing unit.

In various embodiments, the present invention provides a computer system for imaging a sample comprising an infrared or near-infrared fluorophore, comprising: one or more processors and memory to store one or more programs, the one or more programs comprising instructions for: (a) operating an image sensor to detect visible light and infrared light and generate sensor signals at a first frequency, wherein there is no infrared filter in the light path from the sample to the image sensor, and wherein the image sensor comprises blue, green and red pixel sensors; (b) operating a laser to emit an excitation light for the infrared or near-infrared fluorophore and to alternate between on and off statuses at a second frequency, wherein the second frequency is half of the first frequency; (c) operating a first channel to conduct the excitation light from the laser to the sample; (d) operating a light source to emit a light comprising visible light; (e) operating a second channel to conduct the visible light from the light source to the sample; (f) operating a notch beam splitter in the light path from the laser to the sample and in the light path from the sample to the image sensor, whereby the excitation light is reflected by the notch beam splitter to the sample, whereby the excitation light excites the infrared or near-infrared fluorophore in the sample to emit an emission light, and whereby the emission light is transmitted through the notch beam splitter to the image sensor; (g) operating a third channel to conduct the emission light from the sample to the image sensor; (h) operating a fourth channel to conduct the visible light from the sample to the image sensor; (i) operating a notch filter in the light path from the sample to the image sensor, whereby the notch filter blocks the excitation light; (j) operating a synchronization module to synchronize the image sensor with the laser and visible light, whereby a single sensor signal is synchronized to a single on or off status of the laser; (k) operating an image processing unit to process sensor signals to generate image frames, wherein the image processing unit is connected to the image sensor, wherein the image processing unit subtracts an image frame generated when the laser is off from the previous or next image frame generated when the laser is on, whereby an infrared-only image frame is generated upon the difference between the two successive image frames, wherein the image processing unit false colors the infrared-only image frame, wherein the image processing unit adds the false colored infrared-only image frame back to the image frame generated when the laser is off, whereby a composite image frame of visible light and infrared light is generated; and (1) operating an image displaying unit to display images based on the image frames generated from the image processing unit, wherein the image displaying unit is connected to the image processing unit.

In various embodiments, the present invention provides a non-transitory computer-readable storage medium storing one or more programs for imaging a sample comprising an infrared or near-infrared fluorophore, the one or more programs for execution by one or more processors of a computer system, the one or more programs comprising instructions for: (a) operating an image sensor to detect visible light and infrared light and generate sensor signals at a first frequency, wherein there is no infrared filter in the light path from the sample to the image sensor, and wherein the image sensor comprises blue, green and red pixel sensors; (b) operating a laser to emit an excitation light for the infrared or near-infrared fluorophore and to alternate between on and off statuses at a second frequency, wherein the second frequency is half of the first frequency; (c) operating a first channel to conduct the excitation light from the laser to the sample; (d) operating a light source to emit a light comprising visible light; (e) operating a second channel to conduct the visible light from the light source to the sample; (f) operating a notch beam splitter in the light path from the laser to the sample and in the light path from the sample to the image sensor, whereby the excitation light is reflected by the notch beam splitter to the sample, whereby the excitation light excites the infrared or near-infrared fluorophore in the sample to emit an emission light, and whereby the emission light is transmitted through the notch beam splitter to the image sensor; (g) operating a third channel to conduct the emission light from the sample to the image sensor; (h) operating a fourth channel to conduct the visible light from the sample to the image sensor; (i) operating a notch filter in the light path from the sample to the image sensor, whereby the notch filter blocks the excitation light; (j) operating a synchronization module to synchronize the image sensor with the laser and visible light, whereby a single sensor signal is synchronized to a single on or off status of the laser; (k) operating an image processing unit to process sensor signals to generate image frames, wherein the image processing unit is connected to the image sensor, wherein the image processing unit subtracts an image frame generated when the laser is off from the previous or next image frame generated when the laser is on, whereby an infrared-only image frame is generated upon the difference between the two successive image frames, wherein the image processing unit false colors the infrared-only image frame, wherein the image processing unit adds the false colored infrared-only image frame back to the image frame generated when the laser is off, whereby a composite image frame of visible light and infrared light is generated; and (1) operating an image displaying unit to display images based on the image frames generated from the image processing unit, wherein the image displaying unit is connected to the image processing unit.

In various embodiments, the present invention provides a computer implemented method for imaging a sample, comprising: on a device having one or more processors and a memory storing one or more programs for execution by the one or more processors, the one or more programs including instructions for: providing a sample; providing an imaging system of any previous claim; and imaging the sample using the imaging system.

In various embodiments, the present invention provides a computer system for imaging a sample, comprising: one or more processors and memory to store one or more programs, the one or more programs comprising instructions for: providing a sample; providing an imaging system of any previous claim; and imaging the sample using the imaging system.

In various embodiments, the present invention provides a non-transitory computer-readable storage medium storing one or more programs for imaging a sample, the one or more programs for execution by one or more processors of a computer system, the one or more programs comprising instructions for: providing a sample; providing an imaging system of any previous claim; and imaging the sample using the imaging system.

In various embodiments, the present invention provides a computer implemented method for treating a subject with a tumor, comprising: on a device having one or more processors and a memory storing one or more programs for execution by the one or more processors, the one or more programs including instructions for: administering an infrared dye to the subject, thereby labeling the tumor with the infrared dye; performing a surgery on the subject to access the area of the labeled tumor; providing an imaging system of any previous claim; identifying the labeled tumor under the imaging system; and removing the labeled tumor, thereby treating the subject with the tumor.

In various embodiments, the present invention provides a computer system for treating a subject with a tumor, comprising: one or more processors and memory to store one or more programs, the one or more programs comprising instructions for: administering an infrared dye to the subject, thereby labeling the tumor with the infrared dye; performing a surgery on the subject to access the area of the labeled tumor; providing an imaging system of any previous claim; identifying the labeled tumor under the imaging system; and removing the labeled tumor, thereby treating the subject with the tumor.

In various embodiments, the present invention provides a non-transitory computer-readable storage medium storing one or more programs for treating a subject with a tumor, the one or more programs for execution by one or more processors of a computer system, the one or more programs comprising instructions for: administering an infrared dye to the subject, thereby labeling the tumor with the infrared dye; performing a surgery on the subject to access the area of the labeled tumor; providing an imaging system of any previous claim; identifying the labeled tumor under the imaging system; and removing the labeled tumor, thereby treating the subject with the tumor.

In various embodiments, the present invention provides a computer implemented method for capturing and processing images and for smooth image display, comprising: on a device having one or more processors and a memory storing one or more programs for execution by the one or more processors, the one or more programs including instructions for: utilizing parallel process software coding; transferring a raw image; and de-mosaicing the raw image to the one or more processors.

The one or more processors can comprise a graphics processing unit (GPU).

The parallel process software coding can comprise GPU based Computer Unified Device Architecture (CUDA).

The parallel process software coding can be stored directly on a video card.

The raw image can be an 8 bit raw image

The images can comprise full high definition frames at 300 frames per second, a full HD (1080p) 8 bit image can be approximately 2 Mb in size, the PCIe 3.0 data transfer rate can be approximately 7 Gb/s, and the image can be transferred to the GPU in 300 μsec.

After transferring the image to the GPU, an image processing operation can be performed. The image processing operation can be one or more from the group consisting of: Bayer demosaicing, subtracting a scattered light image from a fluorescence image, adding Red, Green and Blue channels of a fluorescence frame, imparting false coloring to a fluorescence image, and adding a white light image with a false colored fluorescence image.

In order to improve speed, instead of returning the image to a system memory for display, openGL/directx functions of the GPU can be used to display a final image.

Images can be displayed on a medical grade HD quality video monitor.

In various embodiments, the present invention provides a computer system for capturing and processing images and for smooth image display, comprising: one or more processors and memory to store one or more programs, the one or more programs comprising instructions for: utilizing parallel process software coding; transferring a raw image; and de-mosaicing the raw image to the one or more processors.

The one or more processors can comprise a graphics processing unit (GPU).

The parallel process software coding can comprise GPU based Computer Unified Device Architecture (CUDA).

The parallel process software coding can be stored directly on a video card.

The raw image can be an 8 bit raw image

The images can comprise full high definition frames at 300 frames per second, a full HD (1080p) 8 bit image can be approximately 2 Mb in size, the PCIe 3.0 data transfer rate can be approximately 7 Gb/s, and the image can be transferred to the GPU in 300 μsec.

After transferring the image to the GPU, an image processing operation can be performed. The image processing operation can be one or more from the group consisting of: Bayer demosaicing, subtracting a scattered light image from a fluorescence image, adding Red, Green and Blue channels of a fluorescence frame, imparting false coloring to a fluorescence image, and adding a white light image with a false colored fluorescence image.

In order to improve speed, instead of returning the image to a system memory for display, openGL/directx functions of the GPU can be used to display a final image.

Images can be displayed on a medical grade HD quality video monitor.

In various embodiments, the present invention provides a non-transitory computer-readable storage medium storing one or more programs for capturing and processing images and for smooth image display, the one or more programs for execution by one or more processors of a storage medium, the one or more programs comprising instructions for: utilizing parallel process software coding; transferring a raw image; and de-mosaicing the raw image to the one or more processors.

The one or more processors can comprise a graphics processing unit (GPU).

The parallel process software coding can comprise GPU based Computer Unified Device Architecture (CUDA).

The parallel process software coding can be stored directly on a video card.

The raw image can be an 8 bit raw image

The images can comprise full high definition frames at 300 frames per second, a full HD (1080p) 8 bit image can be approximately 2 Mb in size, the PCIe 3.0 data transfer rate can be approximately 7 Gb/s, and the image can be transferred to the GPU in 300 μsec.

After transferring the image to the GPU, an image processing operation can be performed. The image processing operation can be one or more from the group consisting of: Bayer demosaicing, subtracting a scattered light image from a fluorescence image, adding Red, Green and Blue channels of a fluorescence frame, imparting false coloring to a fluorescence image, and adding a white light image with a false colored fluorescence image.

In order to improve speed, instead of returning the image to a system memory for display, openGL/directx functions of the GPU can be used to display a final image.

Images can be displayed on a medical grade HD quality video monitor.

In various embodiments, the present invention provides an imaging system for imaging a sample. In accordance with the invention, the sample comprises an infrared or near-infrared fluorophore. The system comprises: an image sensor, a laser, a notch beam splitter, a notch filter, and a synchronization module. The image sensor detects visible light and infrared light and generates sensor signals. The laser emits an excitation light for the infrared or near-infrared fluorophore and alternates between on and off statuses. The notch beam splitter is placed in the light path from the laser to the sample and in the light path from the sample to the image sensor. The excitation light is reflected by the notch beam splitter to the sample; the excitation light excites the infrared or near-infrared fluorophore in the sample to emit an emission light; and the emission light is transmitted through the notch beam splitter to the image sensor. The notch filter is placed in the light path from the sample to the image sensor, and the notch filter blocks the excitation light. The synchronization module synchronizes the image sensor with the laser and visible light, whereby a single sensor signal is synchronized to a single on or off status of the laser. In various embodiments, the imaging system further comprises a fast trigger unit.

In various embodiments, the imaging system further comprises a light source to emit a light comprising visible light. In accordance with the invention, visible light can have a spectrum of 400-700 nm. In some embodiments, there is an infrared filter in the light path from the light source to the sample. In accordance with the invention, the intensity of the laser is controlled to ensure uniform excitation on the same area illuminated by visible light.

In accordance with the invention, the on-off frequency of the laser is half of the frequency of the image sensor generating sensor signals. In various embodiments, the laser alternates between on and off status at a frequency of 60 Hz. In various embodiments, the image sensor generates sensor signals at a frequency of 120 Hz.

In various embodiments, the excitation light comprises light having a wavelength of about 785 nm and/or 780 nm. In various embodiments, the notch beam splitter selectively reflects light having a wavelength of about 785 nm and/or 780 nm. In various embodiments, the notch filter blocks light having a wavelength of about 785 nm and/or 780 nm.

In various embodiments, there is no infrared filter in the light path from the sample to the image sensor. In various embodiments, there is no infrared filter in the light path from the laser to the sample. In some embodiments, there is an optical filter to block the excitation light in the light path from the sample to the image sensor. In other embodiments, there is no optical filter to block the excitation light in the light path from the laser to the sample.

In various embodiments, the imaging system further comprises an image processing unit to process sensor signals to generate image frames. In accordance with the present invention, the image processing unit is connected to the image sensor. In various embodiments, the image processing unit subtracts an image frame generated when the laser is off from the previous or next image frame generated when the laser is on, whereby an infrared-only image frame is generated upon the difference between the two successive image frames. In accordance with the invention, the image processing unit false colors the infrared-only image frame. In accordance with the invention, the image processing unit adds the false colored infrared-only image frame back to the image frame generated when the laser is off, whereby a composite image frame of visible light and infrared light is generated. In some embodiments, the image processing unit generates composite image frames of visible light and infrared light at a frequency of 60 Hz.

In various embodiments, the imaging system further comprises an image displaying unit to display images based on the image frames generated from the image processing unit. In accordance with the present invention, the image displaying unit is connected to the image processing unit. Examples of the image displaying unit include but are not limited to monitors, projectors, phones, tablets, and screens. In some embodiments, the image displaying unit displays composite image frames of visible light and infrared light at a frequency of 60 Hz.

In various embodiments, the imaging system further comprises a first channel to conduct the excitation light from the laser to the sample, a second channel to conduct the visible light from the light source to the sample, a third channel to conduct the emission light from the sample to the image sensor, and a fourth channel to conduct the visible light from the sample to the image sensor. In accordance with the present invention, the first, second, third and fourth channels are four separate channels or combined into one, two, or three channels. Still in accordance with the present invention, two or more of the four channels may overlap partially or completely on their light paths. In various embodiments, the first, second, third and fourth channels are endoscope or microscope.

In various embodiments, the present invention provides an imaging system for imaging a sample. In accordance with the invention, the sample comprises an infrared or near-infrared fluorophore. Still in accordance with the invention, the infrared or near-infrared fluorophore can be a cyanide-based infrared or near-infrared fluorophore (e.g., indocyanine green (ICG)). The system comprises: (a) an image sensor, (b) a laser, (c) a first channel, (d) a light source, (e) a second channel, (f) a notch beam splitter, (g) a third channel, (h) a fourth channel, (i) a notch filter, (j) a synchronization module, (k) an image processing unit, and (l) an image displaying unit. (a) The image sensor detects visible light and infrared light and generates sensor signals at a first frequency. There is no infrared filter in the light path from the sample to the image sensor. The image sensor comprises blue, green and red pixel sensors. Examples of the image sensor include but are not limited to CCD image sensors and CMOS image sensors. (b) The laser emits an excitation light for the infrared or near-infrared fluorophore and alternates between on and off statuses at a second frequency, wherein the second frequency is half of the first frequency. (c) The first channel conducts the excitation light from the laser to the sample. (d) The light source emits a light comprising visible light. (e) The second channel conducts the visible light from the light source to the sample. (f) The notch beam splitter is placed in the light path from the laser to the sample and in the light path from the sample to the image sensor. The excitation light is reflected by the notch beam splitter to the sample; the excitation light excites the infrared or near-infrared fluorophore in the sample to emit an emission light; and the emission light is transmitted through the notch beam splitter to the image sensor. (g) The third channel conducts the emission light from the sample to the image sensor. (h) The fourth channel conducts the visible light from the sample to the image sensor. (i) The notch filter is placed in the light path from the sample to the image sensor, and the notch filter blocks the excitation light. (j) The synchronization module synchronizes the image sensor with the laser and visible light, whereby a single sensor signal is synchronized to a single on or off status of the laser. (k) The image processing unit is connected to the image sensor and processes sensor signals to generate image frames. The image processing unit subtracts an image frame generated when the laser is off from the previous or next image frame generated when the laser is on, whereby an infrared-only image frame is generated upon the difference between the two successive image frames. The image processing unit false colors the infrared-only image frame. The image processing unit adds the false colored infrared-only image frame back to the image frame generated when the laser is off, whereby a composite image frame of visible light and infrared light is generated. (l) The image displaying unit is connected to the image processing unit and displays images based on the image frames generated from the image processing unit.

In various embodiments, the image sensor comprises blue, green and red pixel sensors. In one embodiment, all the blue, green and red pixel sensors are sensitive to both visible light and infrared light. In various embodiments, the image sensor is a CCD image sensor that detects visible light and infrared light and generates CCD image signals. In various embodiments, the image sensor is a CMOS image sensor that detects visible light and infrared light and generates CMOS image signals. In various embodiments, the image sensor is without a NIR long pass filter.

In various embodiments, the present invention provides a method of imaging a sample. The method comprises the steps of: providing a sample, providing an imaging system described herein, and imaging the sample using the imaging system. In further embodiments, the method further comprises a step of performing a surgery on a subject to access the sample or to isolate the sample. In various embodiments, the subject has cancer and may need surgery to remove cancerous tissue, and the sample refers to the body part containing cancerous tissue. In various embodiments, the subject is a human. In various embodiments, the subject is a mammalian subject including but not limited to human, monkey, ape, dog, cat, cow, horse, goat, pig, rabbit, mouse and rat. Still in further embodiments, the method further comprises a step of labeling the sample with an infrared or near-infrared fluorophore. In accordance with the invention, the infrared or near-infrared fluorophore can be indocyanine green (ICG), or any suitable cyanide-based infrared or near-infrared fluorophore. In some embodiments, the various infrared or near-infrared fluorophores described herein may be modified to be more or less lipophilic.

In various embodiments, the present invention also provides a method of treating a subject with a tumor. The method comprises the steps of: administering an infrared dye to the subject, thereby labeling the tumor with the infrared dye; performing a surgery on the subject to access the area of the labeled tumor; providing an imaging system described herein; identifying the labeled tumor under the imaging system; and removing the labeled tumor, thereby treating the subject with the tumor.

The imaging systems and methods of the invention can be used to image a sample from various subjects including but not limited to humans and nonhuman primates such as chimpanzees and other ape and monkey species; farm animals such as cattle, sheep, pigs, goats and horses; domestic mammals such as dogs and cats; laboratory animals including rodents such as mice, rats and guinea pigs, and the like. In various embodiments, the subject has cancer and may need surgery to remove cancerous tissue, and the sample refers to the body part containing cancerous tissue. In various embodiments, the sample is a tumor, cell, tissue, organ, or body part. In some embodiments, the sample is isolated from a subject. In other embodiments, the sample is integral of a subject. In accordance with the invention, the sample comprises an infrared or near-infrared fluorophore.

Examples of the infrared or near-infrared fluorophore include but are not limited to a cyanide-based infrared or near-infrared fluorophore, indocyanine green (ICG), IR800, Alexa680, and cy5.5, and their functional equivalents, analogs, derivatives or salts. In some embodiments, the various infrared or near-infrared fluorophores described herein may be modified to be more or less lipophilic. One of ordinary skill in the art would know how to choose suitable elements in the imaging methods and systems described herein for a particular infrared or near-infrared fluorophore. As one non-limiting example, when the infrared dye to be detected is ICG (excitation 748-789 nm with a peak at 785 nm; emission 814-851 nm with a peak at 825 nm), one of ordinary skill in the art would choose a laser emitting an excitation light of about 785 nm, a laser clean-up filter transmitting light of 775-795 nm, a notch filter blocking light of 770-800 nm, and/or a notch beam splitter splitting light at 700 nm in various systems and methods described herein. It is known that ICG has different peaks in different materials. Also, ICG is a non-limiting example and other fluorophores may be used in place of ICG. One of ordinary skill in the art would understand the settings may be modified accordingly when the peak is not 785 as described in this non-limiting example. For instance, the system may use almost any IR or NIR wavelength by changing the laser excitation and the optical filters.

Typical dosages of an effective amount of the infrared or near-infrared fluorophore can be in the ranges recommended by the manufacturer where known imaging compounds are used, and also as indicated to the skilled artisan by the in vitro results in cells or in vivo results in animal models. Such dosages typically can be reduced by up to about an order of magnitude in concentration or amount without losing relevant labeling activity. The actual dosage can depend upon the judgment of the physician, the condition of the patient, and the effectiveness of the imaging method based, for example, on the in vitro results of relevant cultured cells or histocultured tissue sample, or the in vivo results observed in the appropriate animal models. In various embodiments, the infrared or near-infrared fluorophore may be administered once a day (SID/QD), twice a day (BID), three times a day (TID), four times a day (QID), or more, so as to administer an effective amount of the infrared or near-infrared fluorophore to the subject, where the effective amount is any one or more of the doses described herein.

In various embodiments, the infrared or near-infrared fluorophore is administered to a subject or applied to a sample about 5-10, 10-20, 20-30, or 30-60 minutes before imaging. In various embodiments, the infrared or near-infrared fluorophore is administered to a subject or applied to a sample about 1-6, 6-12, 12-18, 18-24, 24-30, 30-36, 36-42, or 42-48 hours before imaging. In an embodiment, the infrared or near-infrared fluorophore is ICG, or a functional equivalent, analog, derivative or salt of ICG. In other embodiments, the infrared or near-infrared fluorophore is one from the group consisting of: IR800, Alexa680, cy5.5, a functional equivalent of IR800, a functional equivalent of Alexa680, a functional equivalent of cy5.5, an analog of IR800, an analog of Alexa680, an analog of cy5.5, a derivative of IR800, a derivative of Alexa680, a derivative of cy5.5, a salt of IR800, a salt of Alexa 680 or a salt of cy5.5. In certain embodiments, the infrared or near-infrared fluorophore is administered to a human.

In various embodiments, the infrared or near-infrared fluorophore is administered to a subject or applied to a sample at about 0.1-0.5, 0.5-1, 1-1.5, 1.5-2, 2-3, 3-4, 4-5, 5-10, 10-20, 20-50, or 50-100 mg/kg. In various embodiments, the infrared or near-infrared fluorophore is administered to a subject or applied to a sample at about 0.001 to 0.01 mg/kg, 0.01 to 0.1 mg/kg, 0.1 to 0.5 mg/kg, 0.5 to 5 mg/kg, 5 to 10 mg/kg, 10 to 20 mg/kg, 20 to 50 mg/kg, 50 to 100 mg/kg, 100 to 200 mg/kg, 200 to 300 mg/kg, 300 to 400 mg/kg, 400 to 500 mg/kg, 500 to 600 mg/kg, 600 to 700 mg/kg, 700 to 800 mg/kg, 800 to 900 mg/kg, or 900 to 1000 mg/kg. Here, "mg/kg" refers to mg per kg body weight of the subject. In an embodiment, the infrared or near-infrared fluorophore is ICG, or a functional equivalent, analog, derivative or salt of ICG. In other embodiments, the infrared or near-infrared fluorophore is one from the group consisting of: IR800, Alexa680, cy5.5, a functional equivalent of IR800, a functional equivalent of Alexa680, a functional equivalent of cy5.5, an analog of IR800, an analog of Alexa680, an analog of cy5.5, a derivative of IR800, a derivative of Alexa680, a derivative of cy5.5, a salt of IR800, a salt of Alexa 680 or a salt of cy5.5. In certain embodiments, the infrared or near-infrared fluorophore is administered to a human.

In various embodiments, the infrared or near-infrared fluorophore is administered to a subject or applied to a sample once, twice, three or more times. In various embodiments, the infrared or near-infrared fluorophore is administered to a subject or applied to a sample about 1-3 times per day, 1-7 times per week, or 1-9 times per month. Still in some embodiments, the infrared or near-infrared fluorophore is administered to a subject or applied to a sample for about 1-10 days, 10-20 days, 20-30 days, 30-40 days, 40-50 days, 50-60 days, 60-70 days, 70-80 days, 80-90 days, 90-100 days, 1-6 months, 6-12 months, or 1-5 years. In an embodiment, the infrared or near-infrared fluorophore is ICG, or a functional equivalent, analog, derivative or salt of ICG. In certain embodiments, the infrared or near-infrared fluorophore is administered to a human.

In accordance with the invention, the infrared or near-infrared fluorophore may be administered using the appropriate modes of administration, for instance, the modes of administration recommended by the manufacturer. In accordance with the invention, various routes may be utilized to administer the infrared or near-infrared fluorophore of the claimed methods, including but not limited to aerosol, nasal, oral, transmucosal, transdermal, parenteral, implantable pump, continuous infusion, topical application, capsules and/or injections. In various embodiments, the retinoid agonist is administered intravascularly, intravenously, intraarterially, intratumorally, intramuscularly, subcutaneously, intranasally, intraperitoneally, or orally.

In various embodiments, the infrared or near-infrared fluorophore is provides as a pharmaceutical composition. Preferred compositions will also exhibit minimal toxicity when administered to a mammal.

In various embodiments, the pharmaceutical compositions according to the invention may be formulated for delivery via any route of administration. "Route of administration" may refer to any administration pathway known in the art, including but not limited to aerosol, nasal, oral, transmucosal, transdermal, parenteral, enteral, topical or local. "Parenteral" refers to a route of administration that is generally associated with injection, including intraorbital, infusion, intraarterial, intracapsular, intracardiac, intradermal, intramuscular, intraperitoneal, intrapulmonary, intraspinal, intrasternal, intrathecal, intrauterine, intravenous, subarachnoid, subcapsular, subcutaneous, transmucosal, or transtracheal. Via the parenteral route, the compositions may be in the form of solutions or suspensions for infusion or for injection, or as lyophilized powders. Via the parenteral route, the compositions may be in the form of solutions or suspensions for infusion or for injection. Via the enteral route, the pharmaceutical compositions can be in the form of tablets, gel capsules, sugar-coated tablets, syrups, suspensions, solutions, powders, granules, emulsions, microspheres or nanospheres or lipid vesicles or polymer vesicles allowing controlled release. Typically, the compositions are administered by injection. Methods for these administrations are known to one skilled in the art. In accordance with the invention, the pharmaceutical composition may be formulated for intravenous, intramuscular, subcutaneous, intraperitoneal, oral or via inhalation administration.

In various embodiments, the pharmaceutical compositions according to the invention can contain any pharmaceutically acceptable excipient. "Pharmaceutically acceptable excipient" means an excipient that is useful in preparing a pharmaceutical composition that is generally safe, non-toxic, and desirable, and includes excipients that are acceptable for veterinary use as well as for human pharmaceutical use. Such excipients may be solid, liquid, semisolid, or, in the case of an aerosol composition, gaseous. Examples of excipients include but are not limited to starches, sugars, microcrystalline cellulose, diluents, granulating agents, lubricants, binders, disintegrating agents, wetting agents, emulsifiers, coloring agents, release agents, coating agents, sweetening agents, flavoring agents, perfuming agents, preservatives, antioxidants, plasticizers, gelling agents, thickeners, hardeners, setting agents, suspending agents, surfactants, humectants, carriers, stabilizers, and combinations thereof.

In various embodiments, the pharmaceutical compositions according to the invention can contain any pharmaceutically acceptable carrier. "Pharmaceutically acceptable carrier" as used herein refers to a pharmaceutically acceptable material, composition, or vehicle that is involved in carrying or transporting a compound of interest from one tissue, organ, or portion of the body to another tissue, organ, or portion of the body. For example, the carrier may be a liquid or solid filler, diluent, excipient, solvent, or encapsulating material, or a combination thereof. Each component of the carrier must be "pharmaceutically acceptable" in that it must be compatible with the other ingredients of the formulation. It must also be suitable for use in contact with any tissues or organs with which it may come in contact, meaning that it must not carry a risk of toxicity, irritation, allergic response, immunogenicity, or any other complication that excessively outweighs its therapeutic benefits.

The pharmaceutical compositions according to the invention can also be encapsulated, tableted or prepared in an emulsion or syrup for oral administration. Pharmaceutically acceptable solid or liquid carriers may be added to enhance or stabilize the composition, or to facilitate preparation of the composition. Liquid carriers include syrup, peanut oil, olive oil, glycerin, saline, alcohols and water. Solid carriers include starch, lactose, calcium sulfate, dihydrate, terra alba, magnesium stearate or stearic acid, talc, pectin, acacia, agar or gelatin. The carrier may also include a sustained release material such as glyceryl monostearate or glyceryl distearate, alone or with a wax.

The pharmaceutical preparations are made following the conventional techniques of pharmacy involving milling, mixing, granulation, and compressing, when necessary, for tablet forms; or milling, mixing and filling for hard gelatin capsule forms. When a liquid carrier is used, the preparation will be in the form of a syrup, elixir, emulsion or an aqueous or non-aqueous suspension. Such a liquid formulation may be administered directly p.o. or filled into a soft gelatin capsule.

The pharmaceutical compositions according to the invention may be delivered in a therapeutically effective amount. The precise therapeutically effective amount is that amount of the composition that will yield the most effective results in terms of efficacy of labeling a sample in a given subject. This amount will vary depending upon a variety of factors, including but not limited to the characteristics of the labeling compound such as an infrared or near-infrared fluorophore, (including activity, pharmacokinetics, pharmacodynamics, and bioavailability), the physiological condition of the subject (including age, sex, disease type and stage, general physical condition, responsiveness to a given dosage, and type of medication), the nature of the pharmaceutically acceptable carrier or carriers in the formulation, and the route of administration. One skilled in the clinical and pharmacological arts will be able to determine a effective amount for labeling a sample through routine experimentation, for instance, by monitoring a subject's response to administration of a compound and adjusting the dosage accordingly. For additional guidance, see Remington: The Science and Practice of Pharmacy (Gennaro ed. 20th edition, Williams & Wilkins Pa., USA) (2000).

Before administration to a subject, formulants may be added to the composition. A liquid formulation may be preferred. For example, these formulants may include oils, polymers, vitamins, carbohydrates, amino acids, salts, buffers, albumin, surfactants, bulking agents or combinations thereof.

Carbohydrate formulants include sugar or sugar alcohols such as monosaccharides, disaccharides, or polysaccharides, or water soluble glucans. The saccharides or glucans can include fructose, dextrose, lactose, glucose, mannose, sorbose, xylose, maltose, sucrose, dextran, pullulan, dextrin, alpha and beta cyclodextrin, soluble starch, hydroxyethyl starch and carboxymethylcellulose, or mixtures thereof "Sugar alcohol" is defined as a C4 to C8 hydrocarbon having an —OH group and includes galactitol, inositol, mannitol, xylitol, sorbitol, glycerol, and arabitol. These sugars or sugar alcohols mentioned above may be used individually or in combination. There is no fixed limit to amount used as long as the sugar or sugar alcohol is soluble in the aqueous preparation. In one embodiment, the sugar or sugar alcohol concentration is between 1.0 w/v % and 7.0 w/v %, more preferable between 2.0 and 6.0 w/v %. Amino acids formulants include levorotary (L) forms of carnitine, arginine, and betaine; however, other amino acids may be added. In some embodiments, polymers as formulants include polyvinylpyrrolidone (PVP) with an average molecular weight between 2,000 and 3,000, or polyethylene glycol (PEG) with an average molecular weight between 3,000 and 5,000.

It is also preferred to use a buffer in the composition to minimize pH changes in the solution before lyophilization or after reconstitution. Most any physiological buffer may be used including but not limited to citrate, phosphate, succinate, and glutamate buffers or mixtures thereof. In some embodiments, the concentration is from 0.01 to 0.3 molar. Surfactants that can be added to the formulation are shown in EP Nos. 270,799 and 268,110.

Another drug delivery system for increasing circulatory half-life is the liposome. Methods of preparing liposome delivery systems are discussed in Gabizon et al., Cancer Research (1982) 42:4734; Cafiso, Biochem Biophys Acta (1981) 649:129; and Szoka, Ann Rev Biophys Eng (1980) 9:467. Other drug delivery systems are known in the art and are described in, e.g., Poznansky et al., DRUG DELIVERY SYSTEMS (R. L. Juliano, ed., Oxford, N.Y. 1980), pp. 253-315; M. L. Poznansky, Pharm Revs (1984) 36:277.

After the liquid pharmaceutical composition is prepared, it may be lyophilized to prevent degradation and to preserve sterility. Methods for lyophilizing liquid compositions are known to those of ordinary skill in the art. Just prior to use, the composition may be reconstituted with a sterile diluent (Ringer's solution, distilled water, or sterile saline, for example) which may include additional ingredients. Upon reconstitution, the composition is administered to subjects using those methods that are known to those skilled in the art.

The compositions of the invention may be sterilized by conventional, well-known sterilization techniques. The resulting solutions may be packaged for use or filtered under aseptic conditions and lyophilized, the lyophilized preparation being combined with a sterile solution prior to administration. The compositions may contain pharmaceutically-acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, and stabilizers (e.g., 1-20% maltose, etc.).

In some embodiments, the invention described herein is provided with a custom lens solution (e.g., a camera), for example, as a complete system containing all components for usage. In other embodiments, the invention described herein is provided to complement a user's existing equipment, for example, as an add-on system to be used with NIR-capable exoscopes and endoscopes, or to be integrated into operating microscopes.

While various embodiments of the present invention are described in the context of various infrared or near-infrared fluorophores, it should not be construed that the present invention is limited to those infrared or near-infrared fluorophores. In fact, those infrared or near-infrared fluorophores are merely non-limiting examples. Indeed, the present invention may be used for fluorophores in any suitable segment of electromagnetic spectrum, for example, ultraviolet (UV), ultraviolet A, ultraviolet B, ultraviolet C, near ultraviolet, middle ultraviolet, far ultraviolet, hydrogen lyman-alpha, vacuum ultraviolet, extreme ultraviolet, visible, infrared, near infrared, mid infrared, and far infrared. Examples of fluorophores outside the infrared or near-infrared range include but are not limited to fluorescein, sodium yellow, and 5-aminolevulinic acid (5-ALA). While in various embodiments of the present invention, particular types of imaging components (e.g., image sensors, lasers, laser clean-up filters, notch filters, and other associated filters) are described in the context of various infrared or near-infrared fluorophores, it should not be construed that the present invention is limited to those particular imaging components. In fact, those particular imaging components are merely non-limiting examples. Indeed, the present invention also contemplates choosing and including appropriate imaging components (e.g., image sensors, lasers, laser clean-up filters, notch filters, and other associated filters) for the use of those fluorophores outside the infrared or near-infrared range.

EXAMPLES

The following examples are provided to better illustrate the claimed invention and are not to be interpreted as limiting the scope of the invention. To the extent that specific materials are mentioned, it is merely for purposes of illustration and is not intended to limit the invention. One skilled in the art may develop equivalent means or reactants without the exercise of inventive capacity and without departing from the scope of the invention.

Example 1

Figure 2:
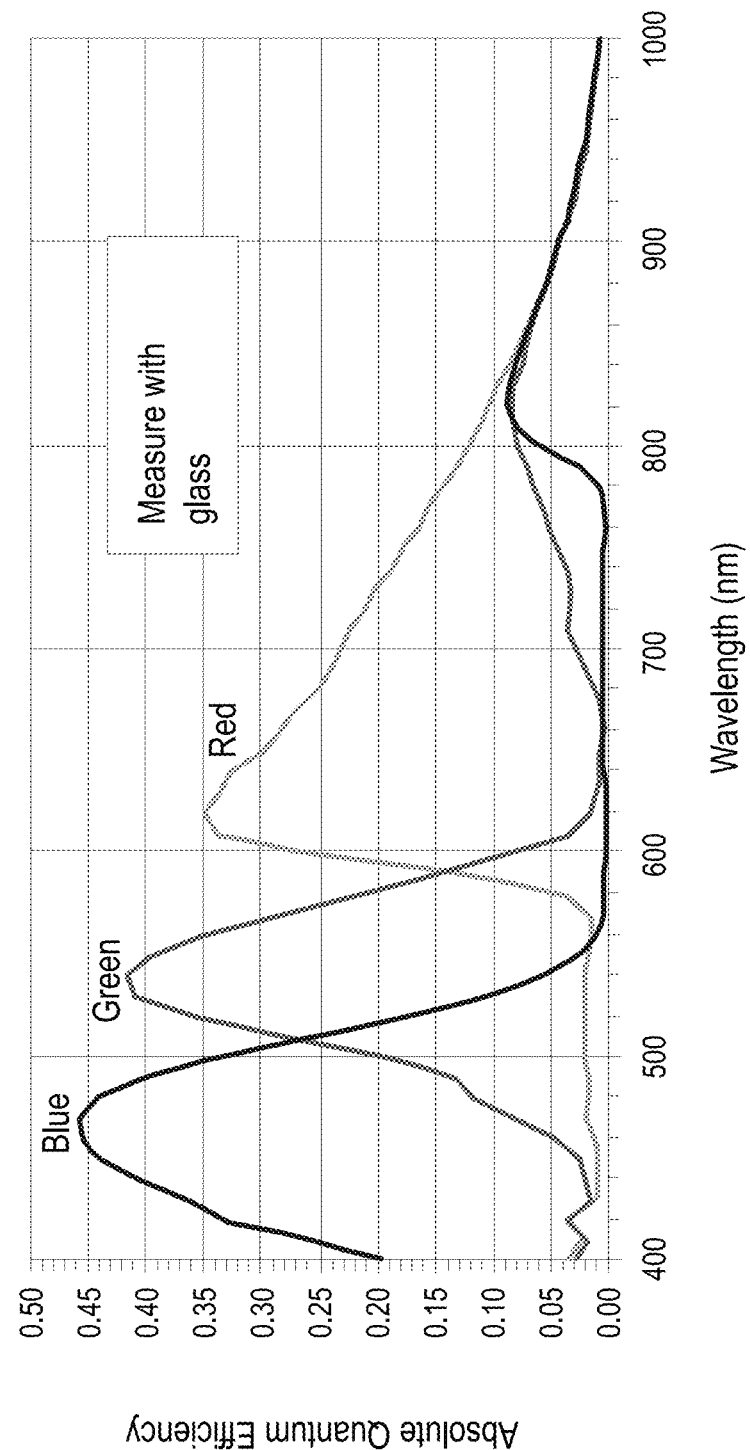
FIG. 2 depicts, in accordance with various embodiments of the present invention, the typical sensitivity of the color sensors.
Figure 3:
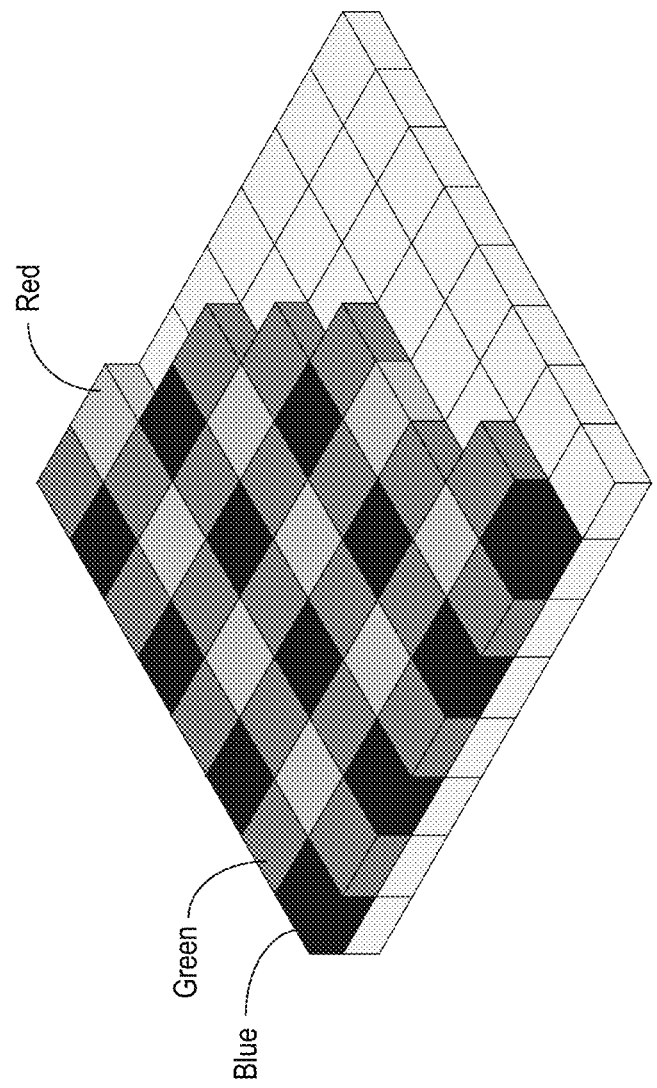
FIG. 3 depicts, in accordance with various embodiments of the present invention, the color filter array over the image sensor.

Charged Coupled Devices (CCDs) or Complementary metal-oxide-semiconductor (CMOS) sensors used in the cameras have a broad spectrum of sensitivity ranging from 400 nm to 1000 nm (FIG. 2). All the Red, Green and Blue sensors show sensitivity in the 800-1000 nm of wavelength. The commercially available cameras have a color filter array (CFA) or color filter mosaic (CFM) as shown in FIG. 3 on top of a sensor to collect color information from the image. In addition to this filter array there is an additional NIR short pass filter to cutoff light from 700-1000 nm of wavelength.

Example 2

Figure 4:
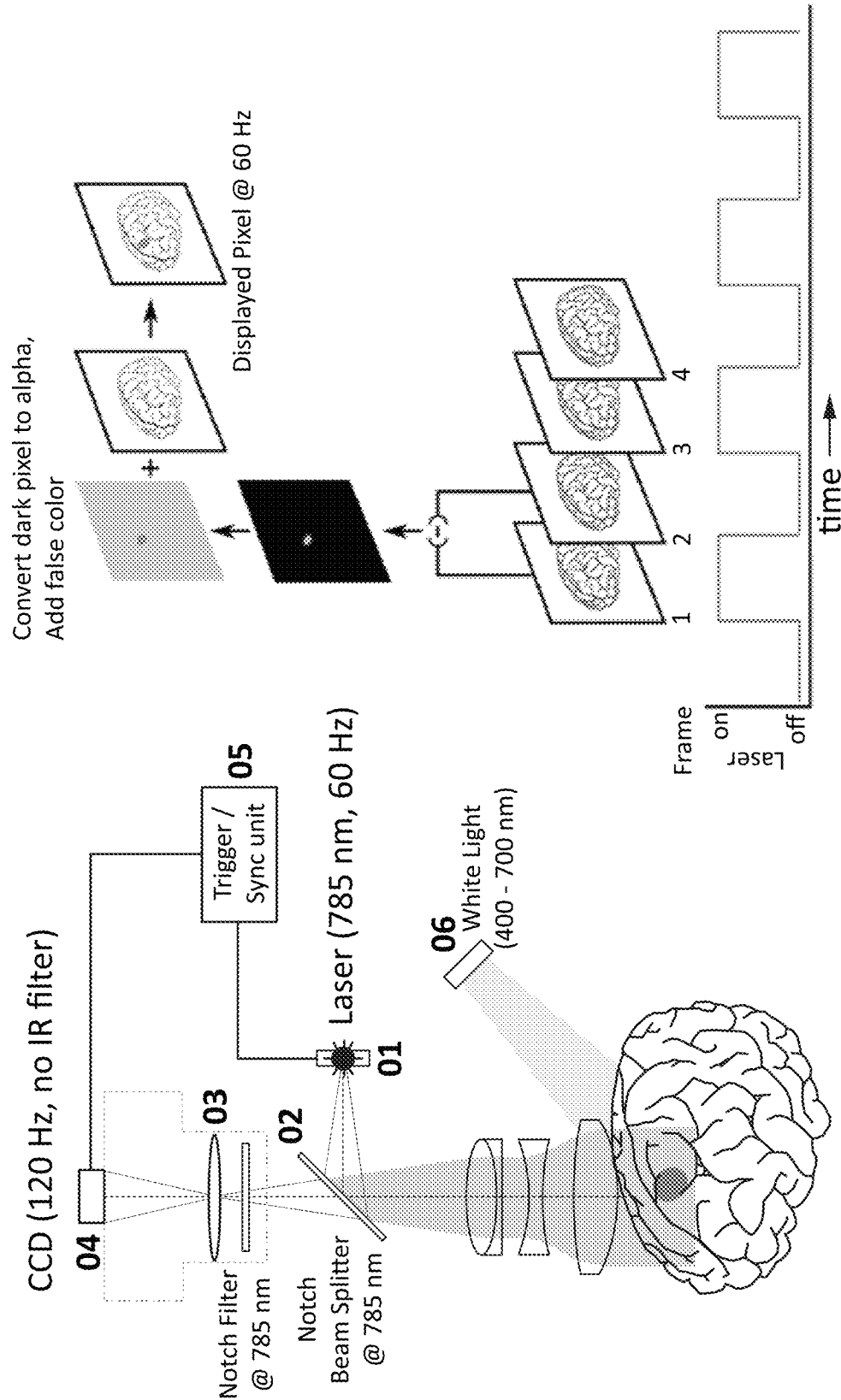
FIG. 4 depicts, in accordance with various embodiments of the present invention, an exemplar system for simultaneously recording visible light image and infrared light image from fluorescent dye. The system comprises a laser 01 with a wavelength of 785 nm, a notch beam splitter @ 785 nm 02, a notch filter @ 785 nm 03, a CCD camera without IR filter 04, and trigger or synchronization unit 05. The laser can alternate between the on and off statues at a frequencies about half the speed of a CCD camera (for example 60 Hz). The CCD camera captures image frames at a frequency of 120 Hz. The synchronization unit synchronizes the CCD image sensor with the laser to ensure that a single image frame corresponds to a single on or off status of the laser. The tissue is tagged with an IR (or NIR) fluorophore. A visible light source 06 illuminates the sample of interest. The wavelength of 785 nm is a non-limiting example, and other wavelengths can also be used with this system.

We use the sensitivity of Red, Green and Blue pixels in near infrared region (NIR) to detect infrared fluorescence. A visible light source illuminates the sample of interest. Also, a laser is used as the excitation light for the infrared fluorophore in tissue, and the emission light from the infrared fluorophore is detected by a CCD camera. Meanwhile, the excitation light is filtered before reaching the CCD camera to avoid interfering detection of the emission light. An image frame is captured when the laser is on (on-frame). Another image frame is captured when the laser is off (off-frame). The on-frame detects both visible light and infrared fluorescence, while the off-frame detects only visible light. Thus, the difference in the intensity between the on-frame and off-frame provides information about the infrared fluorescence signal. (FIG. 4).

1. Excitation:

Excitation is achieved using a very narrow wavelength laser @ NIR wavelength (high absorption) 780 or 785 nm. The laser light is passed through a special lens where the excitation light it is added per focal using a notch beam splitter (e.g. NFD01-785-25x36) (FIG. 4). The laser is turned on and off at half the frequency of the camera frame rate. The laser intensity can be controlled in order to ensure uniform excitation on the same area visible by the camera.

2. Triggering and Synchronizing:

The laser light is triggered using external trigger which is synchronized with image frames captured by the CCD camera. Every frame of the CCD camera is synchronized with turning on and off of the laser (FIG. 4).

Figure 5C:
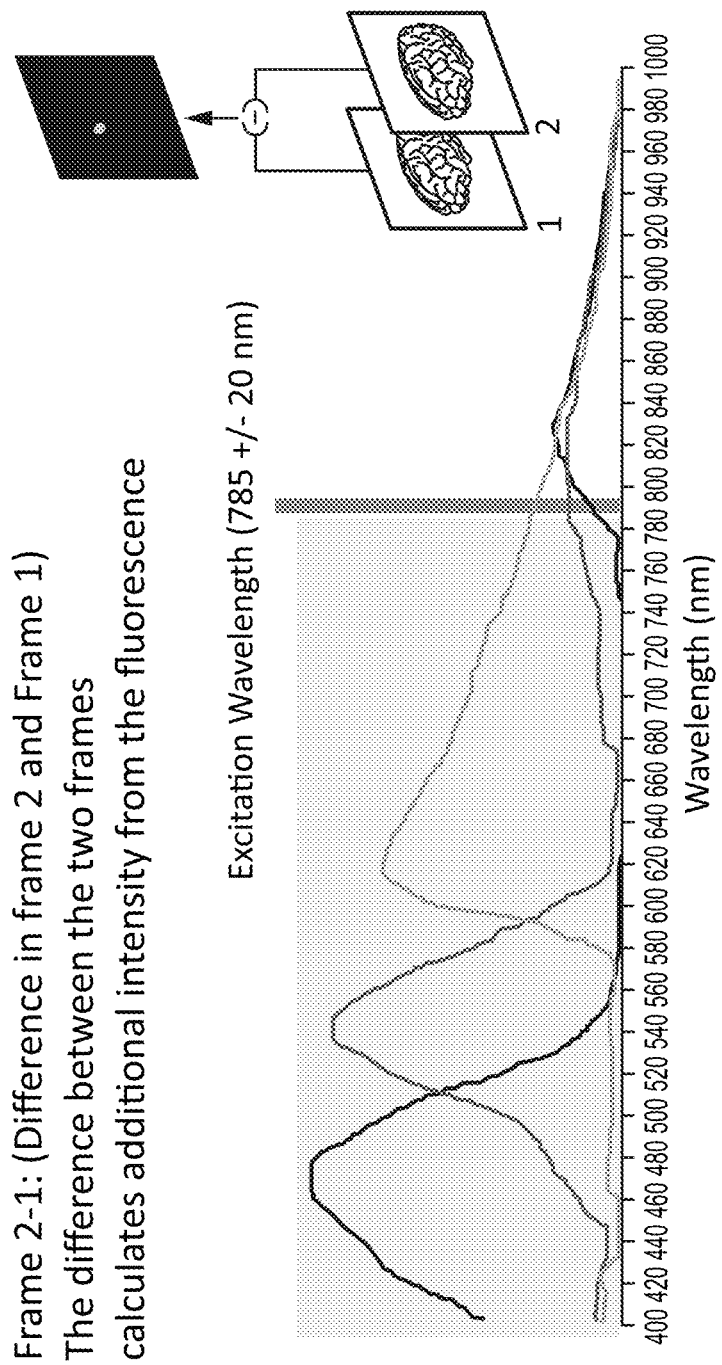

3. CCD:

The frame exposure is controlled using external trigger. As an example, Frame 1 is captured when the laser is off and Frame 2 is captured when the laser is on. Frame 1 captures the normal visible light coming from the tissue (FIG. 5A). Frame 2 captures additional infrared fluorescence (the white window in FIG. 5B). By subtracting Frame 1 from Frame 2, we recover the additional intensity added by infrared fluorescence. This calculated infrared fluorescence can be given a false color and added back into Frame 1 to display a composite image frame of visible light and infrared fluorescence. This process is continuously repeated to display or record a real-time video during a surgical operation.

Example 3

By removing the NIR short pass filter in front of the sensor, it is possible to detect fluorescence light emitted by the NIR fluorophores on all RGB channels (FIG. 2). But in order to differentiate between the visible light and NIR light we have to ensure that there is no visible light on the sensor when capturing an NIR image frame. In order to capture the NIR light, there should not be any visible light. In some situations, we capture one frame when there is no visible light or NIR light, record the light, and then subtract it from the NIR captured frame. A clinical prototype is shown in FIGS. 6A-6C.

Figure 1:
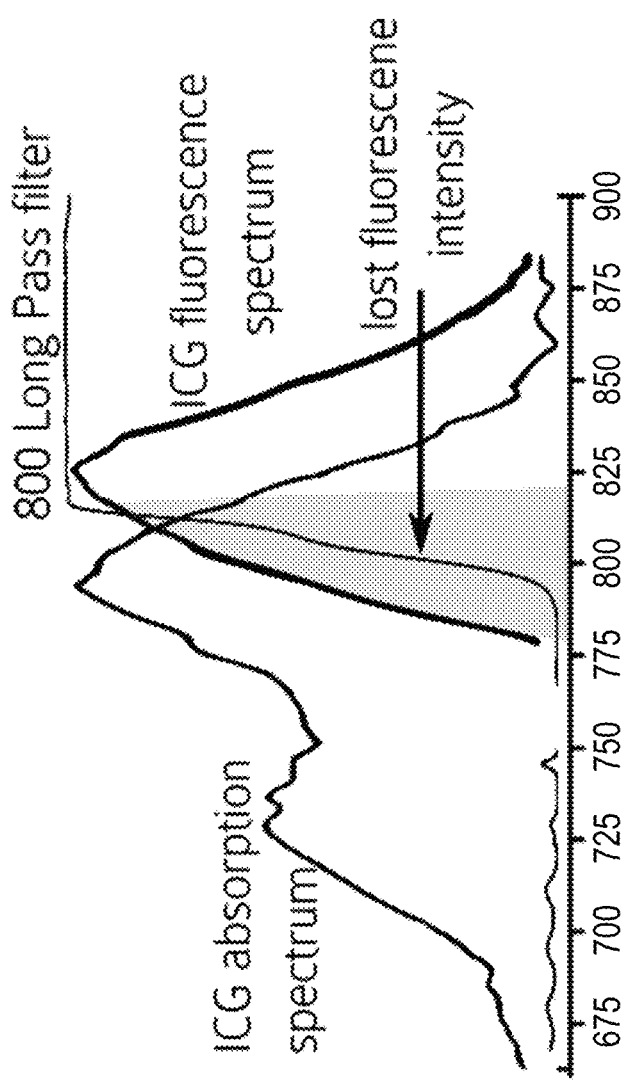
FIG. 1 depicts, in accordance with various embodiments of the present invention, the possible loss of fluorescent light when using of long pass filter for a two camera solution.

1. Filter Combination:

We use a very specific filter combination to achieve highest signal to noise ratio (SNR). Instead of using a broadband excitation as described in most current NIR system, we use an extremely narrow band excitation at 785 nm (optimal for ICG, may vary depending on the fluorophore), the excitation is further narrowed using a laser clean up filter (FIG. 7) and the excitation light from the fluorescence light coming back from the target is removed using a notch filter which is slightly broader than the laser clean up filter. This makes sure that we capture the entire fluorescence signal without losing the fluorescence from the area shaded in FIG. 1.

2. Lens System:

The lens system accomplishes two goals: 1) delivery of the pulsed NIR excitation light and white light to the distal end of the lens to ensure full illumination of the surgical field and reduce the strength of the excitation light in the optical pathway of the emission light. The casing to this lens system has been designed to deliver both NIR and white light to the surgical field in a uniform way. 2) Apochromatic lenses ensure maximal light capture and transmission to the camera, with a built in notch filter (Semrock, 785 nm StopLine® single-notch filter, NF03-785E-25) to remove excitation light.

3. Frame Capture Times:

The frames are captured at very high frame rate of 300 frames per second using a frame grabber. Slower or faster frame rate can also be used. The frame capture and laser strobe (on/off) are synchronized using a multifunction DAQ. This allows us to capture 10 frames for every frame finally displayed (30 fps). The 10 frames are divided in two sets of 5 frames each (FIG. 8). The 5 capture frames are further divided as, 1) first frame is WLF (white light "on", NIR light "off"), 2) the second frame is a SLF (white light "off", NIR light "off"), and 3) the next three frames are NIF (white light "off", NIR light "on"). After subtracting SLF from all three NIFs, The NIF RGB channels are added together, and then the final NIF is given false color before adding it to the WLF. Frames generated from both frames are ultimately added to produce a display frame. This process serves to produce crisp WL and NIR images at a sufficient video rate to seem instantaneous to the surgeon. The exact order of WLF, SLF and NIF can be shuffled.

4. Computer Architecture, Hardware and Software:

To capture and process full HD frames at 300 frames per second, we may rely on parallel processing techniques as even the fastest CPUs available are unlikely able to perform the required video processing calculations at a fast enough rate for smooth image display. In order to perform image processing at this frame rate, we can utilize GPU based Computer Unified Device Architecture (CUDA) parallel process software coding directly on the video card. One of the main limitations of using CUDA programming is the overheads for the transfer of data from the system memory and to the GPU and vice versa. In order to overcome this limitation our algorithm is designed to transfer a raw 8 bit image prior to de-mosaicing to the GPU. A full HD (1080p) 8 bit image is approximately 2 Mb in size. If we consider that the PCIe 3.0 data transfer rate of approximately 7 Gb/s, we can transfer the image to the GPU in 300 µsec. After the image is transferred to the GPU we perform image processing operations such as Bayer demosaicing, subtracting the scattered light image from the fluorescence image, adding the Red, Green and Blue channels of the fluorescence frame, imparting false coloring to the fluorescence image, and finally adding the white light image with the false colored fluorescence image. Lastly, in order to improve the speed further, instead of returning the image to the system memory for display, we use the openGL/directx functions of the GPU to display the final image. Images are displayed on a medical grade HD quality video monitor. We have already demonstrated the capability to acquire high quality versions of these images and regulate appearance utilizing software.

Example 4

In this non-limiting example shown in FIG. 10, an image sensor is mounted at the end of an endoscope for visualizing tumors endoscopic ally or laparoscopically. The endoscope also have light channels carrying both white and NIR light. In front of the image sensor, there can be a lens or a set of lenses capable of transmitting both visible light and NIR fluorescence light. The NIR excitation light will be blocked by a notch filter in front of the lens or set of lenses. The electrical connection to the sensor as well as the fiber optics will be housed inside the endoscope.

The various methods and techniques described above provide a number of ways to carry out the application. Of course, it is to be understood that not necessarily all objectives or advantages described can be achieved in accordance with any particular embodiment described herein. Thus, for example, those skilled in the art will recognize that the methods can be performed in a manner that achieves or optimizes one advantage or group of advantages as taught herein without necessarily achieving other objectives or advantages as taught or suggested herein. A variety of alternatives are mentioned herein. It is to be understood that some preferred embodiments specifically include one, another, or several features, while others specifically exclude one, another, or several features, while still others mitigate a particular feature by inclusion of one, another, or several advantageous features.

Furthermore, the skilled artisan will recognize the applicability of various features from different embodiments. Similarly, the various elements, features and steps discussed above, as well as other known equivalents for each such element, feature or step, can be employed in various combinations by one of ordinary skill in this art to perform methods in accordance with the principles described herein. Among the various elements, features, and steps some will be specifically included and others specifically excluded in diverse embodiments.

Although the application has been disclosed in the context of certain embodiments and examples, it will be understood by those skilled in the art that the embodiments of the application extend beyond the specifically disclosed embodiments to other alternative embodiments and/or uses and modifications and equivalents thereof.

Preferred embodiments of this application are described herein, including the best mode known to the inventors for carrying out the application. Variations on those preferred embodiments will become apparent to those of ordinary skill in the art upon reading the foregoing description. It is contemplated that skilled artisans can employ such variations as appropriate, and the application can be practiced otherwise than specifically described herein. Accordingly, many embodiments of this application include all modifications and equivalents of the subject matter recited in the claims appended hereto as permitted by applicable law. Moreover, any combination of the above-described elements in all possible variations thereof is encompassed by the application unless otherwise indicated herein or otherwise clearly contradicted by context.

All patents, patent applications, publications of patent applications, and other material, such as articles, books, specifications, publications, documents, things, and/or the like, referenced herein are hereby incorporated herein by this reference in their entirety for all purposes, excepting any prosecution file history associated with same, any of same that is inconsistent with or in conflict with the present document, or any of same that may have a limiting affect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

It is to be understood that the embodiments of the application disclosed herein are illustrative of the principles of the embodiments of the application. Other modifications that can be employed can be within the scope of the application. Thus, by way of example, but not of limitation, alternative configurations of the embodiments of the application can be utilized in accordance with the teachings herein. Accordingly, embodiments of the present application are not limited to that precisely as shown and described.

Various embodiments of the invention are described above in the Detailed Description. While these descriptions directly describe the above embodiments, it is understood that those skilled in the art may conceive modifications and/or variations to the specific embodiments shown and described herein. Any such modifications or variations that fall within the purview of this description are intended to be included therein as well. Unless specifically noted, it is the intention of the inventors that the words and phrases in the specification and claims be given the ordinary and accustomed meanings to those of ordinary skill in the applicable art(s).

The foregoing description of various embodiments of the invention known to the applicant at this time of filing the application has been presented and is intended for the purposes of illustration and description. The present description is not intended to be exhaustive nor limit the invention to the precise form disclosed and many modifications and variations are possible in the light of the above teachings. The embodiments described serve to explain the principles of the invention and its practical application and to enable others skilled in the art to utilize the invention in various embodiments and with various modifications as are suited to the particular use contemplated. Therefore, it is intended that the invention not be limited to the particular embodiments disclosed for carrying out the invention.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention.

What is claimed is:

1. An imaging system for imaging a sample comprising an infrared or near-infrared fluorophore, comprising:
   a single image sensor;
   a pulsed laser to emit an excitation light for the infrared or near-infrared fluorophore,
      wherein the excitation light is conducted to the sample along an emission light path in a first direction within a first channel;
      wherein the excitation light excites the infrared or near-infrared fluorophore in the sample to emit an emission light, and
      wherein the emission light is conducted to the image single sensor along the emission light path in a second direction opposite the first direction and overlapping at least partially within the first channel;
   a laser clean-up filter in the light path from the pulsed laser to the sample;
   a notch filter in the emission light path from the sample to the single image sensor,
      wherein the notch filter blocks a portion of the excitation light reflected from the sample towards the image single sensor, and wherein the blocking range of the notch filter is broader than the transmitting range of the laser clean-up filter;
   a white light source to emit a light comprising visible light,
      wherein the visible light is conducted to the sample,
      wherein the sample reflects the visible light,
      wherein the reflected visible light is conducted to the image sensor; and
   an image processing unit to process signals from the single image sensor to generate a white light frame (WLF) when the sample receives only visible light, a stray light frame (SLF) when the sample receives neither visible light nor the excitation light, and two or more near infrared frames (NIFs) when the sample receives only the excitation light to reduce a ghosting effect;
   wherein the single image sensor is configured to detect both the emission light and the visible light from the sample and configured to generate sensor signals, and wherein the image sensor comprises blue, green and red pixel sensors.

2. The imaging system of claim 1, wherein there is no Fabry-Perot etalon, Raman analysis filter wheel, dispersive element, dispersive prism, isosceles prism, diffraction grating, reflection-type diffraction grating, or transmission-type diffraction grating in the emission light path from the sample to the single image sensor.

3. The imaging system of claim 1, wherein the emission light is not dispersed or filtered for Raman band selection in the emission light path from the sample to the single image sensor.

4. The imaging system of claim 1, wherein the single image sensor is configured not to detect Raman scattered light from the sample.

5. The imaging system of claim 1, wherein the infrared or near-infrared fluorophore is any one or more of indocyanine green (ICG), a functional equivalent of ICG, an analog of ICG, a derivative of ICG, a salt of ICG, IR800, Alexa680, cy5.5, a functional equivalent of IR800, a functional equivalent of Alexa680, a functional equivalent of cy5.5, an analog of IR800, an analog of Alexa680, an analog of cy5.5, a derivative of IR800, a derivative of Alexa680, a derivative of cy5.5, a salt of IR800, a salt of Alexa 680, and a salt of cy5.5, or combinations thereof.

6. The imaging system of any one of claims 1-5, wherein the single sensor is synchronized to an on and off status of the laser.

7. The imaging system of claim 1, wherein the white light source is pulsed.

8. The imaging system of claim 1, wherein the single image sensor is a CCD image sensor.

9. The imaging system of claim 1, wherein the single image sensor is a CMOS image sensor.

10. The imaging system of claim 1, wherein the laser clean-up filter is not a spatial filter.

11. The imaging system of claim 1, wherein the excitation light comprises light having a wavelength of about 749-789 or 775-795 nm.

12. The imaging system of claim 1, wherein the laser clean-up filter selectively transmits light having a wavelength of about 749-789 or 775-795 nm.

13. The imaging system of claim 1, wherein the notch filter selectively blocks light having a wavelength of about 749-789, 770-800, 765-805, or 760-810 nm.

14. The imaging system of claim 1, further comprising a notch beam splitter in the light path from the pulsed laser to the sample, whereby the excitation light is reflected by the notch beam splitter to the sample.

15. The imaging system of claim 1, further comprising a notch beam splitter in the light path from the white light source to the sample, whereby the visible light is transmitted to the sample.

16. The imaging system of claim 1, further comprising a notch beam splitter that reflects light having a wavelength of about 700, 725, or 750 nm.

17. The imaging system of claim 1, wherein the image processing unit is connected to the single image sensor.

18. The imaging system of claim 17, wherein the image processing unit subtracts the SLF from each NIF and then adds together all SLF-subtracted NIFs to generate a final NIF.

19. The imaging system of claim 18, wherein the image processing unit false colors the final NIF.

20. The imaging system of claim 19, wherein the image processing unit adds the false colored final NIF to the WLF to generate a composite image frame of visible light and infrared light.

21. The imaging system of claim 17, further comprising an image displaying unit to display images based on the image frames generated from the image processing unit, wherein the image displaying unit is connected to the image processing unit.

22. The imaging system of claim 1, wherein the excitation light from the pulsed laser is conducted to the sample through one or more channels, and/or wherein the visible light from the white light source is conducted to the sample through one or more channels, and/or wherein the emission light emitted from the sample is conducted to the single image sensor through one or more channels, and/or wherein the visible light reflected from the sample is conducted to the single image sensor through one or more channels.

23. The imaging system of claim 1,
wherein the excitation light from the pulsed laser is further conducted to the sample through a third light channel housed in an endoscope;
wherein the visible light from the white light source is conducted to the sample through a fourth light channel housed in the endoscope; and
wherein the single image sensor is housed in the endoscope at or near the patient end of the endoscope.

24. The imaging system of claim 23, wherein the third light channel is an optical cable.

25. The imaging system of claim 23, wherein the fourth light channel is an optical cable.

26. The imaging system of claim 23, further comprising one or more lenses in the emission light path and/or the visible light path from the sample to the single image sensor, wherein the one or more lenses are located at or near the patient end of the endoscope.

27. A method for imaging a sample comprising an infrared or near-infrared fluorophore, comprising:
operating a pulsed laser to emit an excitation light for the infrared or near-infrared fluorophore;
conducting the excitation light to the sample along an emission light path in a first direction within a first channel to excite the infrared or near-infrared fluorophore in the sample to emit an emission light;
conducting the emission light to a single image sensor along the emission light path in a second direction opposite the first direction and overlapping at least partially within the first channel;
operating a laser clean-up filter in the light path from the pulsed laser to the sample;
operating a notch filter in the emission light path from the sample to the single image sensor to block a portion of the excitation light reflected from the sample towards the single image sensor, wherein the blocking range of the notch filter is broader than the transmitting range of the laser clean-up filter;
operating a white light source to emit a light comprising visible light;
conducting the visible light to the sample, wherein the sample reflects the visible light;
conducting the reflected visible light to the single image sensor;
operating the single image sensor to detect both the emission light and the visible light from the sample and to generate sensor signals, wherein the single image sensor comprises blue, green and red pixel sensors; and
operating an image processing unit to process signals from the single image sensor to generate a white light frame (WLF) when the sample receives only visible light, a stray light frame (SLF) when the sample receives neither visible light nor the excitation light, and two or more near infrared frames (NIFs) when the sample receives only the excitation light to reduce a ghosting effect.

28. The method of claim 27, further comprising performing a surgery on a subject to access the sample or to isolate the sample.

29. The method of any one of claims 27-28, further comprising labeling the sample with the infrared or near-infrared fluorophore.

30. The method of claim 27, wherein the infrared or near-infrared fluorophore is any one or more of indocyanine green (ICG), a functional equivalent of ICG, an analog of ICG, a derivative of ICG, a salt of ICG, IR800, Alexa680, cy5.5, a functional equivalent of IR800, a functional equivalent of Alexa680, a functional equivalent of cy5.5, an analog of IR800, an analog of Alexa680, an analog of cy5.5, a derivative of IR800, a derivative of Alexa680, a derivative of cy5.5, a salt of IR800, a salt of Alexa 680, and a salt of cy5.5, or combinations thereof.

31. The imaging system of claim 1, wherein operating the laser clean-up filter narrows the wavelength band of the excitation light to a peak absorption band of the infrared or near-infrared fluorophore, and wherein the narrowed excitation light excites the infrared or near-infrared fluorophore in the sample to emit the emission light.

32. The imaging system of claim 1, wherein there is no infrared filter in the emission light path from the sample to the single image sensor.

33. The imaging system of claim 1, wherein the single image sensor comprises one or more image sensors.

34. The imaging system of claim 15, wherein the visible light from the white light source is conducted to the sample through a third channel, wherein the emission light emitted from the sample is conducted to the single image sensor through the second channel, and wherein the visible light reflected from the sample is conducted to the single image sensor through a fourth channel.

35. The imaging system of claim 34, wherein the first, second, third, and fourth channels are four separate channels or combined into one, two, or three channels.

36. The imaging system of claim 18, wherein the image processing unit generates the WLF from a first frame, the SLF from a second frame captured after the first frame, and the NIF from a third frame captured after the second frame.

37. The imaging system of claim 36, wherein the image processing unit generates the NIF from the third frame, a fourth frame captured after the third frame, and a fifth frame captured after the fourth frame.

38. The imaging system of claim 37, wherein the image processing unit generates the image frame by adding together two subsequent sets of the first frame, the second frame, the third frame, the fourth frame, and the fifth frame.

\* \* \* \* \*